(12) United States Patent
Li et al.

(10) Patent No.: US 8,252,835 B2
(45) Date of Patent: Aug. 28, 2012

(54) COMPOUNDS AND METHODS FOR TREATING ESTROGEN RECEPTOR-RELATED DISEASES

(75) Inventors: Jin Li, Pawcatuck, CT (US); Kun Meng, Hong Kong (CN)

(73) Assignee: Shenogen Pharma Group Ltd., Beijing (CN)

( * ) Notice: Subject to any disclaimer, the term of this patent is extended or adjusted under 35 U.S.C. 154(b) by 4 days.

(21) Appl. No.: 11/877,575

(22) Filed: Oct. 23, 2007

(65) Prior Publication Data

US 2008/0146658 A1 Jun. 19, 2008

Related U.S. Application Data

(60) Provisional application No. 60/862,984, filed on Oct. 25, 2006.

(51) Int. Cl.
*A61K 31/35* (2006.01)
*A61K 31/70* (2006.01)
*A01N 43/16* (2006.01)

(52) U.S. Cl. .......... 514/456; 514/27; 514/783; 549/400; 549/403; 546/112; 536/8; 424/195.11

(58) Field of Classification Search .......... 514/456, 514/27, 783; 549/400, 403; 424/195.11; 546/112; 536/8
See application file for complete search history.

(56) References Cited

U.S. PATENT DOCUMENTS

| 6,750,248 B2 | 6/2004 | Yong et al. |
| 2003/0170292 A1 | 9/2003 | Yong |
| 2005/0049206 A1 | 3/2005 | Gong et al. |
| 2005/0136140 A1 | 6/2005 | Chou |

FOREIGN PATENT DOCUMENTS

| CN | 03129242 | | 6/2003 |
| CN | 1460482 A | | 12/2003 |
| WO | 9947137 | * | 9/1999 |
| WO | 02/13842 A1 | | 2/2002 |

OTHER PUBLICATIONS

Curtis et al, PNAS, Jul. 22, 2003, vol. 100, issue 15 9023-9027.*
Ross et al, Science, 1973, vol. 180, p. 1332-1339.*
Pasqualine et al, Hormone-Dependent Cancer, Copyright 1996 by Marcel Dekker, Inc.*
Wilkinson, Pharmacokinetics, Chapter 1, in Goodman and Gilman's "the pharmacological basis of Therapeutics" 10th edition, Copyright 2001.*
Gura (Science, vol. 278, pp. 1041-1042 (1997).*
Booth (Nature's Review, Drug discovery, vol. 2, pp. 609-610 (2003.*
Cos et al (Planta Med, 2003, vol. 69, pp. 589-599.*

(Continued)

*Primary Examiner* — Savitha Rao
(74) *Attorney, Agent, or Firm* — Jun He Law Offices P.C.; James J. Zhu

(57) ABSTRACT

Provided herein in certain embodiments are compounds, pharmaceutical compositions and methods for modulating the functions of estrogen receptor alpha 36, for preventing and/or treating diseases related to estrogen receptor alpha 36, for preventing and/or treating respiratory diseases such as asthma, for inducing cell death and/or inhibiting cell proliferation and for preventing and/or treating diseases involving abnormal cell proliferation such as cancers.

14 Claims, 20 Drawing Sheets

OTHER PUBLICATIONS

Adlercreutz (Journal of steroid biochemistry and Molecular biology, 2003, vol. 83, pp. 113-118) further teach that phytoestrogen consumption is not or only slightly protective with regard to breast cancer (see abstract.*
Ingle et al. (Breast Cancer Res. 2002, vol. 4, pp. 133-136).*
Schafer et al. Drug Discovery Today 2008, 13 (21/22), 913-916.*
Horig et al. Journal of Translational Medicine 2004, 2(44).*
PCT International Search Report for PCT/US07/82286 dated Mar. 7, 2008 (2 pages).
Berge et al., "Pharmaceutical Salts," J. Pharm. Sci., 66:1-19 (1977).
Flouriot, G. et al., "Identification of a new isoform of the human estrogen receptor-alpha (hER-alpha) that is encoded by distinct transcripts and that is able to repress hER-alpha activation function 1," EMBO, 19:4688-4700 (2000).
Li et al., "Plasma membrane localization and function of the estrogen receptor a variant (ER46) in human endothelial cells," Proc. Natl. Acad. Sci. USA 100:4807-4812 (2003).
Jian, Liu et al., "Determination of rat urinary metabolites of icariin in vivo and estrogenic activities of its metabolites on MCF-7 cells," Pharmazie 60:120-125 (2005).
Nikaido et al., "Inhibition of adenosine 3', 5'-cyclic monophosphate phosphodiesterase by flavonoids, III," Chem. Pharm. Bull. 1989, 37:1392.
Wang et al., "A variant of estrogen receptor-{alpha}, hER-{alpha}36: Transduction of estrogen- and antiestrogen-dependent membrane-initiated mitogenic signaling," Proc. Natl. Acad. Sci. U.S.A. 103:9063-9068 (2006).
Wang et al., "Identification, cloning, and expression of human estrogen receptor-alpha36, a novel variant of human estrogen receptor-alpha66," Biochem. Biophys. Res. Commun. 336:1023-1027 (2005).
Wang et al., "Proliferation-stimulating effects of icaritin and desmethylicaritin in MCF-7 cells," Europ. J. Pharm. 504:147-153 (2004).
Wu et al., "Chemical and pharmacological investigations of Epimedium species: a survey," Prog Drug Res. 60:1-57 (2003).
Ye et al., "Estrogenic effects of two derivatives of icariin on human breast cancer MCF-7 cells," Phytomedicine 12:735-741 (2005).
Yu, L. J.; HY, Y. Z., "Studies on the synthesis of bavachin," China Pharm. J. 40:1029 (2005).
Lacroix, Marc and Leclercq, Guy, "Relevance of breast cancer cell lines as models for breast tumours: an update", Breast Cancer Research and Treatment (2004) 83:249-289.
Wang Z. Q. et al., "Prenylflavonoids as nonsteroidal phytoestrogens and related structure-activity relationships," Chemmedchem 1:482-488 (2006).
Kitaoka M. et al., "Prenylfavonoids: a new class of non-steroidal phytoestrogen (part 1). Isolation of 8-isopentenylnaringenin and an initial study on its structure-activity relationship," Planta Medica 64:511-515 (1998).
Mori A. et al., "Cytotoxicity of plant flavanoids against HeLa cells," Phytochemistry 27:1017-1020 (1988).
Myers J. R. et al., "Should supplemental estrogens be used as steroid-sparing agents in asthmatic women?" Chest 106:318-319 (1994).
Resnick M., "Estrogen, SERMS reduce asthma impact by halting constriction," Retrieved from the Internet: URL: www.eurekalert.com/pub_releases/2005-04/asp-esr033105.php (retrieved on Jun. 25, 2010).
Chandler M. H. H. et al., "Premenstrual asthma: the effect of estrogen on symptoms, pulmonary function, and beta2-receptors," Pharmacotherapy 17:224-234 (1997).
Nikolic D et al., "Metabloism of 8-prenylnaringenin, a potent phytoestrogen from hops (humulus lupulus), by human liver microsomes," Drug Metabolism and Disposition 32:272-279 (2004). Database WPI Week 200420, Thomson Scientific, London, GB; AN 2004-204155.
Supplementary European search report for European patent application No. EP 07844555 dated Jul. 15, 2010 (14 pages).

* cited by examiner

COMPOUNDS AND METHODS FOR TREATING ESTROGEN RECEPTOR-RELATED DISEASES

CROSS-REFERENCE TO RELATED APPLICATION

The present application claims the benefit of U.S. Provisional Patent Application No. 60/862,984 filed on Oct. 25, 2006, which is incorporated herein by reference in its entirety.

FIELD OF THE INVENTION

The present invention relates to compounds, pharmaceutical compositions and methods for preventing and/or treating estrogen receptor-related diseases.

BACKGROUND

Estrogens are a group of hormones that are involved in many critical physiological functions in the human body. Estrogen functions include developing the female sex organs, preparing the breast and uterus for pregnancy and breast feeding after childbirth. Estrogens also play important roles in maintaining proper cardiovascular function and bone density. Estrogens are known to stimulate cell proliferation and may increase a woman's risk of developing cancers, especially breast cancer and uterus cancer.

Estrogens bind to estrogen receptors in target cells to regulate cell functions. Two types of estrogen receptors were discovered in human cells, hER-α and hER-β. They share common protein structures, each possessing three independent but interacting functional domains: the N-terminal domain (A/B domain), the central DNA-binding domain (C domain), and the C-terminal ligand-binding domain (D/E/F domain). The N-terminal domain has a ligand-independent activation function (AF-1), which is involved in interaction with co-activators and transcriptional activation of target genes in the absence of ligands. The DNA binding-domain plays important roles in receptor dimerization and binding to specific DNA sequences. The C-terminal ligand binding-domain mediates ligand binding and has a ligand-dependent transactivation function (AF-2), activating gene transcription in the presence of ligands.

The full-length hER-α was identified as a 66 kDa protein and referred to as hER-α66. hER-α66 contains all three functional domains. A splice variant of hER-α66 was later discovered and named hER-α46. hER-α46 has a molecular weight of about 46 KDa and lacks the N-terminal AF-1 domain of hER-α66. Recently, a novel 36 kDa hER-α variant, hER-α36, was identified. It lacks the N-terminal AF-1 domain and the C-terminal AF-2 domain of hER-α66 (Wang et al., *Biochem. Biophys. Res. Commun.* 336, 1023-1027 (2005)).

hER-α66 is believed to mediate estrogen-stimulated cell proliferation via transcriptional activation of its target genes. Binding of estrogen to hER-α66 activates the transactivation domain of hER-α66 and thus stimulates the expression of downstream target genes and eventually leads to cell proliferation. hER-α46 was found to mediate membrane-initiated and estrogen-stimulated rapid NO synthesis (Li et al., Proc. Natl. Acad. Sci. USA 100: 4807-4812 (2003)). It was also shown that hER-α46, that lacks the AF-1 domain, inhibits the AF-1 activity of hER-α66 (Flouriot, G., EMBO, 19, 4688-4700 (2000)). Since hER-α36 lacks both the AF-1 and AF-2 transcriptional activation domains, it functions as a dominant-negative inhibitor of hER-α66 and hER-β to inhibit both AF-1 and AF-2 functions of hER-α and hER-β. In addition, hER-α36 is localized primarily on the plasma membrane and mediates membrane-initiated mitogenic estrogen signaling that stimulates cell proliferation. (Wang et al., *Biochem. Biophys. Res. Commun.* 336, 1023-1027 (2005); Wang et al., *Proc. Natl. Acad. Sci. U.S.A.* 103: 9063-9068 (2006)).

Extensive studies have shown that estrogen signaling is mediated via the classic nuclear transcriptional activation pathways as well as the non-classic membrane-initiated signaling pathways. It seems that hER-α66 and hER-α46 function primarily in the nucleus while hER-α36 functions mainly outside of the nucleus.

It was also shown that hER-α36 lacks Helix 8-12 of the ligand-binding domain of the original hER-α66, which totally changes the ligand binding specificity of hER-α36. Thus, hER-α36 may bind to different ligands from hER-α66 and hER-β.

*Epimedium* plants contain estrogen-like compounds that act either as agonists or antagonists. Several different species of *Epimedium* were used as herbal medicines in Traditional Chinese medicines for thousands of years. *Epimedium* herbs were used to treat a wide variety of diseases such as impotence, spermatorrhea, urination problems, lassitude and soreness of loin and knees, infertility in women, amenorrhea, geriatric depression, rheumatic arthritis, cardiovascular failure, hypertension, chronic bronchitis, angina pectoris etc. (Wu et al., Chemical and pharmacological investigations of *Epimedium* species: a survey, *Prog Drug Res.* 60:1-57 (2003)). It was reported that mixture extracted from *Epimedium* herbs may also reduce the risk of hormone-related cancers (U.S. 20030170292). However, it is not clear which ingredients of *Epimedium* herbs may have that function.

Over twenty species of *Epimedium* have been found and characterized and more than 130 different compounds have been identified from *Epimedium* plants (Wu et al., Chemical and pharmacological investigations of *Epimedium* species: a survey, *Prog Drug Res.* 60:1-57 (2003)). The compounds from *Epimedium* plants are mainly flavonoid glycodies, flavones and icarisides. Examples of compounds isolated from *Epimedium* plants are apigenin, brevicornin, icariin, kaempferol, luteolin, quercetin and so on.

Icariin is a flavonoid glycoside compound isolated from *Epimedium* plants. Icariin was shown to have no effect on cell proliferation in vitro. However, two in vivo metabolites of icariin, icaritin and desmethylicaritin, were found to significantly increase proliferation of breast cancer cells (Liu et al., Pharmazie 60: 120-125 (2005); Wang et al., *Europ. J. Pharm.* 504: 147-153 (2004); Ye et al., Phytomedicine 12: 735-741 (2005); CN03129242).

As estrogen and estrogen receptor related diseases continue to affect many individuals, there remains an urgent need to discover novel compounds and methods useful to prevent and/or treat such diseases.

SUMMARY

One embodiment of the invention provides compounds, derivatives thereof, pharmaceutical compositions and methods for modulating the functions of the novel estrogen receptor variant, ER-α36. Another embodiment of the invention provides compounds, derivatives thereof, pharmaceutical compositions and methods for preventing and/or treating diseases related to ER-α36. Another embodiment of the invention provides compounds, derivatives thereof, pharmaceutical compositions and methods for inducing cell death and/or inhibiting cell proliferation, and for preventing and/or treating diseases involving abnormal cell proliferation such as cancer. Further, another embodiment of the present invention provides compounds, derivatives thereof, pharmaceutical compositions and methods for preventing and/or treating asthma and other respiratory diseases.

Certain embodiments of the invention provide compounds for modulating the function of ER-α36. Certain embodiments of the invention provide methods of modulating the function of ER-α36 using the compounds of the invention. Certain embodiments of the invention provide methods of preventing and or treating a disease related to the functions of ER-α36.

Certain embodiments of the invention provide compounds for inducing cell death. Certain embodiments of the invention provide methods of inducing cell death using the compounds of the invention.

Certain embodiments of the invention provide compounds for inhibiting cell proliferation. Certain embodiments of the invention provide methods of inhibiting cell proliferation using the compounds of the invention.

Certain embodiments of the invention provide compounds for preventing and/or treating a disease involving abnormal cell proliferation. Certain embodiments of the invention provide methods of preventing and/or treating a disease involving abnormal cell proliferation in a subject using the compounds of the invention.

Certain embodiments of the invention provide compounds for preventing and/or treating asthma and other respiratory diseases. Certain embodiments of the invention provide methods of preventing and/or treating asthma and other respiratory diseases in a subject using the compounds of the invention.

Certain embodiments of the present invention provide pharmaceutical compositions comprising the compounds of the invention.

DETAILED DESCRIPTION

The Compounds and Derivatives Thereof

Figure 1:
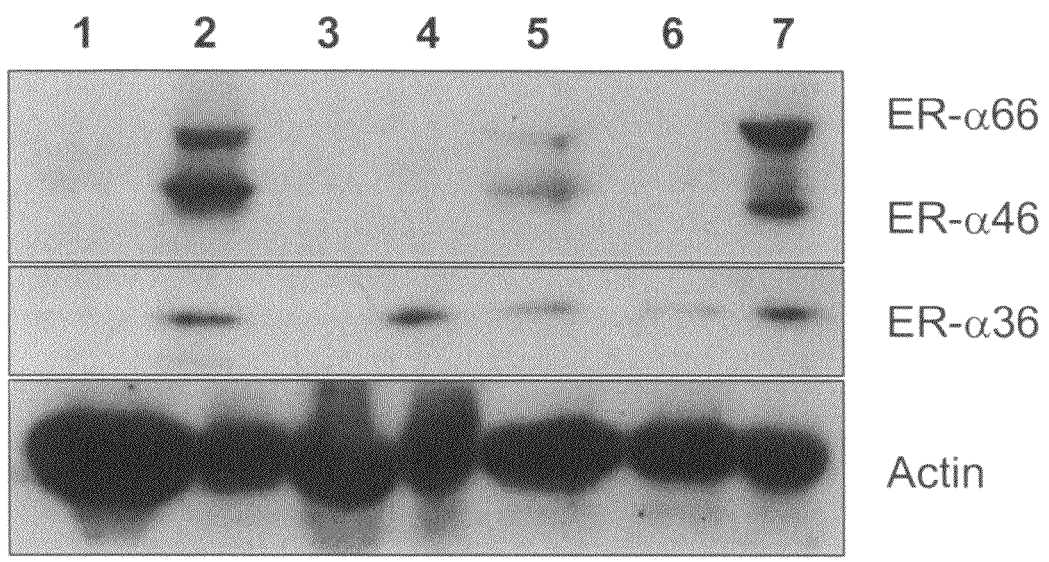
FIG. 1 shows Western blot results depicting the expression of ER-α66, ER-α46 and ER-α36 in human breast cancer samples. Lane 1: normal breast tissue; Lane 2: infiltrating ductal carcinoma; Lane 3: infiltrating ductal carcinoma; Lane 4: invasive ductal carcinoma; Lane 5: infiltrating lobular carcinoma; Lane 6: infiltrating lobular carcinoma; Lane 7: non-invasive ductal carcinoma.

Provided herein in certain embodiments are compounds, derivatives thereof, and pharmaceutical compositions useful for modulating the functions of the novel estrogen receptor, ER-α36, preventing and/or treating diseases related to ER-α36, inducing cell death, inhibiting cell proliferation, preventing and/or treating diseases involving abnormal cell proliferation such as cancer, and/or preventing and/or treating asthma and other respiratory diseases.

In certain embodiments, compounds of Formula (I):

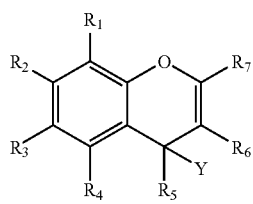

(I)

a stereoisomer or prodrug thereof, or a pharmaceutically acceptable salt of said compound, stereoisomer, or prodrug, are provided wherein:

$R_1$, $R_2$, $R_3$, $R_4$, $R_6$ and $R_7$ are independently hydrogen, halo, hydroxyl, amino, —$SO_3H$ or its salt (including but not limit to —$SO_3Na$, —$SO_3K$, —$SO_3Ca_{1/2}$, —$SO_3Mg_{1/2}$), ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkyl-(C=O)—, formyl, formamidyl, cyano, nitro, HO—(C=O)—, ($C_1$-$C_6$)alkoxycarbonyl, aminocarbonyl, amino($C_1$-$C_6$)alkyl, N—($C_1$-$C_6$)alkylaminocarbonyl, N,N—[($C_1$-$C_6$)alkyl]$_2$-aminocarbonyl, N—($C_6$-$C_{10}$)arylaminocarbonyl, N,N—[($C_6$-$C_{10}$)aryl]$_2$-aminocarbonyl, N—($C_1$-$C_6$)alkyl-N—($C_1$-$C_6$)alkylaminocarbonyl, N—($C_1$-$C_6$)alkyl-N—($C_6$-$C_{10}$)arylaminocarbonyl, ($C_6$-$C_{10}$)aryl (including substituted aryl), ($C_6$-$C_{10}$)aryloxy, ($C_5$-$C_8$)heteroaryl (including substituted heteroaryl), ($C_5$-$C_8$)heteroaryloxy, morpholino-carbonyl, ($C_1$-$C_6$)alkoxyaminocarbonyl, ($C_1$-$C_6$)alkyl-carbonylamino, ($C_3$-$C_8$)cycloalkyl, ($C_3$-$C_8$)cycloalkyl-methyl, ($C_3$-$C_8$)heterocycloalkyl, ($C_3$-$C_8$)heterocycloalkyl-methyl, or $R_1$ and $R_2$ together are —$CH_2CH_2C(CH_3)_2O$—, and $R_3$, $R_4$, $R_6$ and $R_7$ are defined as above.

While Y is hydrogen, $R_5$ is hydrogen, halo, hydroxyl, amino, ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkyl-(C=O)—, formyl, formamidyl, cyano, nitro, HO—(C=O)—, ($C_1$-$C_6$)alkoxycarbonyl, aminocarbonyl, amino($C_1$-$C_6$)alkyl, N—($C_1$-$C_6$)alkylaminocarbonyl, N,N—[($C_1$-$C_6$)alkyl]$_2$-aminocarbonyl, N—($C_6$-$C_{10}$)arylaminocarbonyl, N,N—[($C_6$-$C_{10}$)aryl]$_2$-aminocarbonyl, N—($C_1$-$C_6$)alkyl-N—($C_1$-$C_6$)alkylaminocarbonyl, N—($C_1$-$C_6$)alkyl-N—($C_6$-$C_{10}$)arylaminocarbonyl, ($C_6$-$C_{10}$)aryl, ($C_6$-$C_{10}$)aryloxy, ($C_5$-$C_8$)heteroaryl, ($C_5$-$C_8$)heteroaryloxy, morpholino-carbonyl, ($C_1$-$C_6$)alkoxyaminocarbonyl, ($C_1$-$C_6$)alkyl-carbonylamino, ($C_3$-$C_8$)cycloalkyl, ($C_3$-$C_8$)cycloalkyl-methyl, ($C_3$-$C_8$)heterocycloalkyl, ($C_3$-$C_8$)heterocycloalkyl-methyl or Y and $R_5$ together is oxo (=O).

When $R_1$, $R_2$, $R_3$, $R_4$, $R_5$, $R_6$ or $R_7$ is ($C_1$-$C_6$)alkyl group, each carbon atom of the ($C_1$-$C_6$)alkyl group may be optionally substituted with one to three substituents independently selected from hydroxyl, halo, ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkyl-(C=O)—, formyl, formamidyl, cyano, nitro, HO—(C=O)—, ($C_1$-$C_6$)alkoxycarbonyl, aminocarbonyl, amino($C_1$-$C_6$)alkyl, N—($C_1$-$C_6$)alkylaminocarbonyl, N,N—[($C_1$-$C_6$)alkyl]$_2$-aminocarbonyl, N—($C_6$-$C_{10}$)arylaminocarbonyl, N,N—[($C_6$-$C_{10}$)aryl]$_2$-aminocarbonyl, N—($C_1$-$C_6$)alkyl-N—($C_1$-$C_6$)alkylaminocarbonyl, N—($C_1$-$C_6$)alkyl-N—($C_6$-$C_{10}$)arylaminocarbonyl, ($C_6$-$C_{10}$)aryl, ($C_6$-$C_{10}$)aryloxy, ($C_5$-$C_8$)heteroaryl, ($C_5$-$C_8$)heteroaryloxy, morpholino-carbonyl, ($C_1$-$C_6$)alkoxyaminocarbonyl, ($C_1$-$C_6$)alkyl-carbonylamino, ($C_3$-$C_8$)cycloalkyl, ($C_3$-$C_8$)cycloalkyl-methyl, ($C_3$-$C_8$)heterocycloalkyl, ($C_3$-$C_8$)heterocycloalkyl-methyl.

One embodiment of the present invention includes a group of compounds of Formula (I) referred to as the IA1 group of compounds, wherein said group of compounds have the formula:

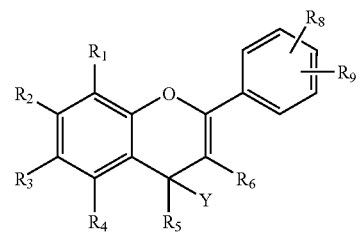

IA1

Wherein $R_8$ and $R_9$ are independently hydrogen, halo, hydroxyl, amino, ($C_1$-$C_6$)alkyl, ($C_2$-$C_6$)alkenyl, ($C_2$-$C_6$)alkynyl, ($C_1$-$C_6$)alkoxy, ($C_1$-$C_6$)alkyl-(C=O)—, formyl, formamidyl, cyano, —$SO_3H$ and its salts (including but not limited to —$SO_3Na$, $SO_3K$, $SO_3Ca_{1/2}$, $SO_3Mg_{1/2}$), nitro, HO—(C=O)—, ($C_1$-$C_6$)alkoxycarbonyl, aminocarbonyl, amino($C_1$-$C_6$)alkyl.

$R_1$, $R_2$, $R_3$, $R_4$, $R_5$, $R_6$, Y are as defined above.

Another embodiment of the present invention includes a group of compounds of Formula (I) referred to as the IA2 group of compounds, wherein said group of compounds have the formula:

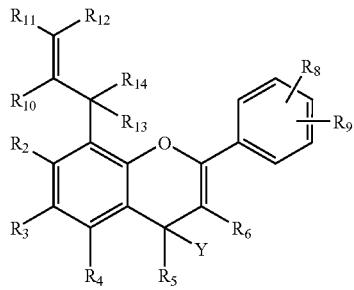

IA2

Wherein $R_{10}$, $R_{11}$, $R_{12}$ are independently hydrogen, halo, $(C_1-C_6)$alkyl, $(C_2-C_6)$alkenyl, $(C_2-C_6)$alkynyl, $(C_1-C_6)$alkoxy, cyano, nitro.

$R_{13}$ and $R_{14}$ are independently hydrogen, $(C_1-C_6)$ alkyl, $(C_2-C_6)$alkenyl, $(C_2-C_6)$alkynyl, $(C_1-C_6)$alkoxy or together as oxo (=O).

$R_2$, $R_3$, $R_4$, $R_5$, $R_6$, $R_8$, $R_9$, Y are as defined above.

Another embodiment of the present invention includes a group of compounds of Formula (I) referred to as the IA3 group of compounds, wherein said group of compounds have the formula:

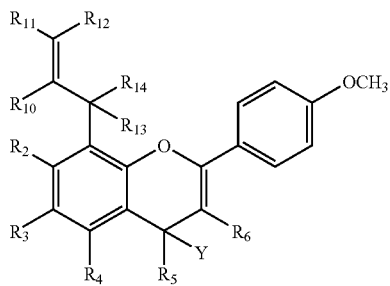

IA3

$R_2$, $R_3$, $R_4$, $R_5$, $R_6$, $R_{10}$, $R_{11}$, $R_{12}$, $R_{13}$, $R_{14}$, Y are as defined above.

Another embodiment of the present invention includes a group of compounds of Formula (I) referred to as the IA4 group of compounds, wherein said group of compounds have the formula:

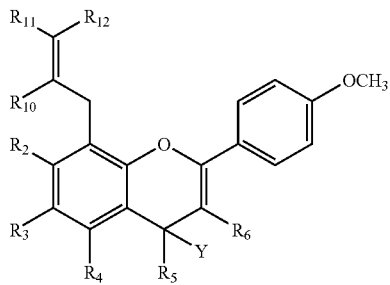

IA4

Wherein $R_2$, $R_3$, $R_4$, $R_5$, $R_6$, $R_{10}$, $R_{11}$, $R_{12}$ and Y are as defined above.

Another embodiment of the present invention includes a group of compounds of Formula (I) referred to as the IA5 group of compounds, wherein said group of compounds have the formula:

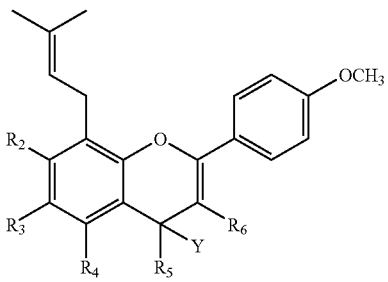

IA5

Wherein $R_2$, $R_3$, $R_4$, $R_5$, $R_6$ and Y are as defined above.

Another embodiment of the present invention includes a group of compounds of Formula (I) referred to as the IA6 group of compounds, wherein said group of compounds have the formula:

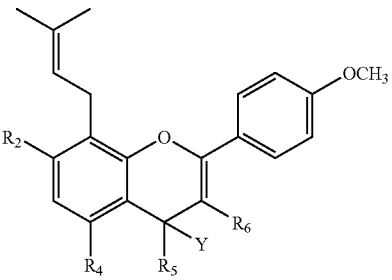

IA6

Wherein $R_2$ is —$SO_3H$ or its salts, —OH or its salts
$R_4$ is —OH or its salts
$R_5$ and Y together is oxo (=O)
$R_6$ is —OH or its salts.

Examples of specific preferred compounds of Formula (I) include but are not limited to the following:

5,7-dihydroxy-2-(8-(2-hydroxy-3-methylbut-3-enyl)-2,2-dimethyl-2H-chromen-6-yl)-4H-chromen-4-one;

5,7-dihydroxy-2-(4-hydroxy-3-(2-hydroxy-3-methylbut-3-enyl)-5-(4-methylpent-3-enyl)phenyl)-4H-chromen-4-one;

5,7-dihydroxy-2-(8-hydroxy-2,2-dimethyl-2H-chromen-6-yl)-4H-chromen-4-one;

5,7-dihydroxy-2-(2,2-dimethyl-2H-chromen-6-yl)-4H-chromen-4-one;

5,7-dihydroxy-2-(4-hydroxy-3-(4-methylpent-3-enyl)phenyl)-4H-chromen-4-one;

3,5,7-trihydroxy-2-(4-hydroxyphenyl)-8-(3-methylbut-2-enyl)-4H-chromen-4-one;

3,5,7-trihydroxy-2-(4-methoxyphenyl)-8-(3-methylbut-2-enyl)-4H-chromen-4-one;

2-(3-amino-4-methoxyphenyl)-3,5-dihydroxy-8-((3,3-dimethyloxiran-2-yl)methyl)-4-oxo-4H-chromen-7-yl hydrogen sulfate;

3,5-dihydroxy-2-(4-methoxyphenyl)-8-(3-methylbut-2-enyl)-4-oxo-4H-chromen-7-yl hydrogen sulfate;

3,5-dihydroxy-2-(4-methoxy-3-nitrophenyl)-8-(3-methylbut-2-enyl)-4-oxo-4H-chromen-7-yl hydrogen sulfate;

2-(3-amino-4-methoxyphenyl)-3,5-dihydroxy-8-(3-methylbut-2-enyl)-4-oxo-4H-chromen-7-yl hydrogen sulfate;
3,5-dihydroxy-2-(4-methoxyphenyl)-8-((3,3-dimethyloxiran-2-yl)methyl)-4H-chromen-4-one;
3,5-dihydroxy-2-(4-methoxy-3-nitrophenyl)-8-((3,3-dimethyloxiran-2-yl)methyl)-4-oxo-4H-chromen-7-yl hydrogen sulfate;
3,5-dihydroxy-8-(2,3-dihydroxy-3-methylbutyl)-2-(4-methoxyphenyl)-4-oxo-4H-chromen-7-yl hydrogen sulfate;
3,5-dihydroxy-8-(2,3-dihydroxy-3-methylbutyl)-2-(4-methoxy-3-nitrophenyl)-4-oxo-4H-chromen-7-yl hydrogen sulfate;
2-(3-amino-4-methoxyphenyl)-3,5-dihydroxy-8-(2,3-dihydroxy-3-methylbutyl)-4-oxo-4H-chromen-7-yl hydrogen sulfate;
5,7-dihydroxy-2-(4-methoxyphenyl)-8-(3-methylbut-2-enyl)-4H-chromen-4-one;
5,7-dihydroxy-2-(4-hydroxyphenyl)-8-(3-methylbut-2-enyl)-4H-chromen-4-one;
2,3-dihydro-5,7-dihydroxy-2-(4-hydroxyphenyl)-8-(3-methylbut-2-enyl)chromen-4-one;
7-hydroxy-2-(4-hydroxyphenyl)-8-(3-methylbut-2-enyl)-4H-chromen-4-one;
5,7-dihydroxy-2-(3,4-dihydroxyphenyl)-4H-Chromen-4-one;
(2S)-2,3-dihydro-7-hydroxy-2-(4-hydroxyphenyl)-6-(3-methyl-2-butenyl)-4H-1-benzopyran-4-one;
(2S)-2,3-dihydro-2-(4-hydroxyphenyl)-7-methoxy-6-(3-methyl-2-butenyl)-4H-1-benzopyran-4-one;
3,5-dihydroxy-2-(4-hydroxyphenyl)-8,8-dimethyl-9,10-dihydro-4H,8H-pyrano[2,3-f]chromen-4-one (herein also referred to as Y4);
3,5-dihydroxy-2-(4-methoxyphenyl)-8,8-dimethyl-9,10-dihydro-4H,8H-pyrano[2,3-f]chromen-4-one;
3,5,7-trihydroxy-8-(3-hydroxy-3-methylbutyl)-2-(4-hydroxyphenyl)-4H-chromen-4-one;
3,5,7-trihydroxy-8-(3-hydroxy-3-methylbutyl)-2-(4-methoxyphenyl)-4H-chromen-4-one (herein also referred to as IC 163).

The compounds and derivatives provided herein may be named according to either the IUPAC (International Union for Pure and Applied Chemistry) or CAS (Chemical Abstracts Service, Columbus, Ohio) nomenclature systems.

The carbon atom content of the various hydrocarbon-containing moieties herein may be indicated by a prefix designating the minimum and maximum number of carbon atoms in the moiety, for example, the prefix $(C_a-C_b)$alkyl indicates an alkyl moiety of the integer "a" to "b" carbon atoms, inclusive. Thus, for example, $(C_1-C_6)$alkyl refers to an alkyl group of one to six carbon atoms inclusive.

The term "alkoxy" refers to straight or branched, monovalent, saturated aliphatic chains of carbon atoms bonded to an oxygen atom. Examples of alkoxy groups include methoxy, ethoxy, propoxy, butoxy, iso-butoxy, tert-butoxy, and the like.

The term "alkyl" refers to straight or branched, monovalent, saturated aliphatic chains of carbon atoms and includes, for example, methyl, ethyl, propyl, isopropyl, butyl, isobutyl, pentyl, isopentyl, hexyl, and the like.

The term "alkenyl" denotes a straight or branched-chain hydrocarbon having one or more double bonds and includes, for example, vinyl, allyl, and the like.

The term "aryl" denotes a cyclic, aromatic hydrocarbon. Examples of aryl groups include phenyl, naphthyl, anthracenyl, phenanthrenyl, and the like.

The term "cycloalkyl" denotes a saturated monocyclic or polycyclic cycloalkyl group, optionally fused to an aromatic hydrocarbon group. Examples of cycloalkyl groups include cyclopropyl, cyclobutyl, cyclopentyl, cyclohexyl, cycloheptyl, indanyl, tetrahydronaphthalinyl, and the like.

The term "halogen" or "halo" represents chloro, bromo, fluoro, and iodo atoms.

The term "heteroaryl" denotes a monocyclic or polycyclic aromatic hydrocarbon group wherein one or more carbon atoms have been replaced with heteroatoms such as nitrogen, oxygen, or sulfur. If the heteroaryl group contains more than one heteroatom, the heteroatoms may be the same or different. Examples of heteroaryl groups include benzofuranyl, benzothienyl, benzimidazolyl, benzoxazolyl, benzothiazolyl, chromenyl, furyl, imidazolyl, indazolyl, indolizinyl, indolyl, isobenzofuranyl, isoindolyl, isoquinolyl, isothiazolyl, isoxazolyl, naphthyridinyl, oxadiazolyl, oxazinyl, oxazolyl, phthalazinyl, pteridinyl, purinyl, pyranyl, pyrazinyl, pyrazolyl, pyridazinyl, pyrido[3,4-b]indolyl, pyridyl, pyrimidyl, pyrrolyl, quinolizinyl, quinolyl, quinoxalinyl, thiadiazolyl, thiatriazolyl, thiazolyl, thienyl, triazinyl, triazolyl, xanthenyl, and the like.

The term "heterocycloalkyl" denotes a saturated monocyclic or polycyclic cycloalkyl group, optionally fused to an aromatic hydrocarbon group, in which at least one of the carbon atoms have been replaced with a heteroatom such as nitrogen, oxygen, or sulfur. If the heterocycloalkyl group contains more than one heteroatom, the heteroatoms may be the same or different. Examples of such heterocycloalkyl groups include azabicycloheptanyl, azetidinyl, indolinyl, morpholinyl, piperazinyl, piperidyl, pyrrolidinyl, tetrahydrofuryl, tetrahydroquinolinyl, tetrahydroindazolyl, tetrahydroindolyl, tetrahydroisoquinolinyl, tetrahydropyranyl, tetrahydroquinoxalinyl, tetrahydrothiopyranyl, thiazolidinyl, thiomorpholinyl, thioxanthenyl, thioxanyl, and the like.

A cyclic group may be bonded to another group in more than one way. If no particular bonding arrangement is specified, then all possible arrangements are intended. For example, the term "pyridyl" includes 2-, 3-, or 4-pyridyl, and the term "thienyl" includes 2- or 3-thienyl.

The term "oxo", means a carbonyl group formed by the combination of a carbon atom(s) and an oxygen atom(s).

The term "prodrug" refers to a compound that is a drug precursor which, following administration to a subject, releases the drug in vivo via a chemical or physiological process (e.g., upon being brought to physiological pH or through enzyme activity). A discussion of the synthesis and use of prodrugs is provided by T. Higuchi and W. Stella, in "Prodrugs as Novel Delivery Systems," vol. 14 of the ACS Symposium Series, and in Bioreversible Carriers in Drug Design, ed. Edward B. Roche, American Pharmaceutical Association and Pergamon Press, 1987, both of which are incorporated herein by reference. The term "prodrug" may include a metabolic precursor of a compound of the invention. The prodrug may be inactive when administered to a subject but is converted in vivo to a compound of the invention. The prodrug can be naturally existing compounds or synthetic compounds.

In certain embodiments, the invention includes prodrugs that can be converted in vivo into 3,5,7-trihydroxy-2-(4-hydroxyphenyl)-8-(3-methylbut-2-enyl)-4H-chromen-4-one, 3,5,7-trihydroxy-2-(4-methoxyphenyl)-8-(3-methylbut-2-enyl)-4H-chromen-4-one, 3,5,7-trihydroxy-8-(3-hydroxy-3-methylbutyl)-2-(4-hydroxyphenyl)-4H-chromen-4-one or 3,5,7-trihydroxy-8-(3-hydroxy-3-methylbutyl)-2-(4-methoxyphenyl)-4H-chromen-4-one. Such prodrugs and their in vivo metabolites are included in the invention.

Examples of prodrugs of the invention include but are not limited to the following:

3-[(6-deoxy-a-L-mannopyranosyl)oxy]-7-(b-D-glucopyra-
nosyloxy)-5-hydroxy-2-(4-methoxyphenyl)-8-(3-methyl-
2-butenyl)-4H-1-benzopyran-4-one;
7-(b-D-glucopyranosyloxy)-3,5-dihydroxy-2-(4-methox-
yphenyl)-8-(3-methyl-2-butenyl)-4H-1-benzopyran-4-
one;
3-[(6-deoxy-a-L-mannopyranosyl)oxy]-5,7-dihydroxy-2-(4-
methoxyphenyl)-8-(3-methyl-2-butenyl)-4H-1-benzopy-
ran-4-one;
3-[[4-O-acetyl-3-O-(6-O-acetyl-b-D-glucopyranosyl)-6-
deoxy-a-L-mannopyranosyl]oxy]-7-(b-D-glucopyranosy-
loxy)-5-hydroxy-2-(4-methoxyphenyl)-8-(3-methyl-2-
butenyl)-4H-1-benzopyran-4-one;
3-[(6-deoxy-2-O-b-D-glucopyranosyl-a-L-mannopyrano-
syl)oxy]-5,7-dihydroxy-2-(4-methoxyphenyl)-8-(3-me-
thyl-2-butenyl)-4H-1-benzopyran-4-one;
2-[4-[(6-deoxy-a-L-mannopyranosyl)oxy]phenyl]-3,5,7-tri-
hydroxy-8-(3-methyl-2-butenyl)-4H-1-benzopyran-4-
one;
3,5-dihydroxy-2-(4-methoxyphenyl)-8-(3-methylbut-2-
enyl)-7-[(2R,3R,4S,5R,6R)-3,4,5-trihydroxy-6-(hy-
droxymethyl)oxan-2-yl]oxy-chromen-4-one;
3-[(2S,3R,4R,5S,6S)-4,5-dihydroxy-6-methyl-3-[(2S,3R,
4R,5S,6S)-3,4,5-trihydroxy-6-methyl-oxan-2-yl]oxy-
oxan-2-yl]oxy-5-hydroxy-2-(4-methoxyphenyl)-8-(3-me-
thylbut-2-enyl)-7-[(2S,3R,4S,5R,6R)-3,4,5-trihydroxy-6-
(hydroxymethyl)oxan-2-yl]oxy-chromen-4-one;

The above listed prodrugs and their in vivo metabolites are included in the invention.

The phrase "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "salts" and "pharmaceutically acceptable salts" refers to organic and inorganic salts of a compound of Formula (I), or a stereoisomer, or prodrug thereof. These salts can be prepared in situ during the final isolation and purification of a compound, or by separately reacting a compound of Formula (I), or a stereoisomer, or prodrug thereof, with a suitable organic or inorganic acid or base and isolating the salt thus formed. Representative salts include the hydrobromide, hydrochloride, sulfate, bisulfate, nitrate, acetate, oxalate, besylate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. For additional examples see, for example, Berge, et al., J. Pharm. Sci., 66, 1-19 (1977), which is incorporated herein by reference.

A salt of a compound of Formula (I) may be readily prepared by mixing together solutions of a compound of Formula (I) and the desired acid or base, as appropriate. The salt may precipitate from solution and be collected by filtration or may be recovered by evaporation of the solvent.

The term "substituted" means that a hydrogen atom on a molecule has been replaced with a different atom or molecule. The atom or molecule replacing the hydrogen atom is denoted as a "substituent."

The compounds of Formula (I) may contain asymmetric or chiral centers and, therefore, exist in different stereoisomeric forms. It is intended that all stereoisomeric forms of the compounds of Formula (I) as well as mixtures thereof, including racemic mixtures, form part of the present invention. In addition, all geometric and positional isomers are also contemplated. For example, if a compound of Formula (I) incorporates a double bond, both the cis- and trans-forms, as well as mixtures thereof, are embraced within the scope of the invention.

Diasteriomeric mixtures can be separated into their individual diastereomers on the basis of their physical chemical differences by methods well-known to those of ordinary skill in the art, such as by chromatography and/or fractional crystallization. Enantiomers can be separated by converting the enantiomeric mixture into a diasteriomeric mixture by reaction with an appropriate optically active compound (e.g., alcohol), separating the diasteriomers and converting (e.g., hydrolyzing) the individual diasteriomers to the corresponding pure enantiomers. Also, some of the compounds of Formula (I) may be atropisomers (e.g., substituted biaryls) and are also considered as part of the invention.

The compounds of Formula (I) may exist in unsolvated as well as solvated forms with pharmaceutically acceptable solvents, such as water, ethanol, and the like, and it is intended that the invention embrace both solvated and unsolvated forms.

It is also possible that the compounds of Formula (I) may exist as tautomeric isomers in equilibrium, and all such forms are embraced within the scope of the invention.

In certain embodiments, isotopically-labeled compounds of Formula (I), which are identical to those recited herein, but for the fact that one or more atoms are replaced by an atom having an atomic mass or mass number different from the atomic mass or mass number usually found in nature are provided. Examples of isotopes that can be incorporated into compounds of Formula (I) include isotopes of hydrogen, carbon, nitrogen, oxygen, phosphorus, fluorine, and chlorine, such as $^2$H, $^3$H, $^{13}$C, $^{14}$C, $^{15}$N, $^{17}$O, $^{18}$O, $^{31}$P, $^{32}$P, $^{35}$S, $^{18}$F, and $^{36}$Cl, respectively. The compounds of Formula (I), the stereoisomers and prodrugs thereof, and the pharmaceutically acceptable salts of the compounds, stereoisomers, or prodrugs, that contain the aforementioned isotopes and/or other isotopes of the other atoms are intended to be within the scope of the instant invention.

Certain isotopically-labeled compounds of Formula (I), for example those compounds into which radioactive isotopes such as $^3$H and $^{14}$C are incorporated, are useful in compound and/or substrate tissue distribution assays. Tritiated, i.e., $^3$H, and carbon-14, i.e., $^{14}$C, isotopes are particularly preferred for their relative ease of preparation and facile detection. Furthermore, substitution with heavier isotopes such as deuterium, i.e., $^2$H, may afford certain therapeutic advantages resulting from greater metabolic stability, for example, increased in vivo half-life, or reduced dosage requirements and, hence, may be preferred in some circumstances. The isotopically-labeled compounds of Formula (I) can generally be prepared by methods known to one of ordinary skill in the art, such as by substituting an isotopically-labeled reagent for a non-isotopically-labeled reagent.

Methods of Use

In certain embodiments, the compounds of the invention are selective modulators of ER-α36 and are useful for modulating the functions of ER-α36 in cells in vitro and in vivo. The compounds are also useful for preventing and/or treating diseases associated with the functions of ER-α36. In certain embodiments, the compounds of the invention can induce cell death and/or inhibit cell proliferation and therefore are useful for preventing and/or treating diseases involving abnormal cell proliferation. In certain embodiments, the compounds of the invention are useful for preventing and/or treating asthma and other respiratory diseases.

In certain embodiments, methods of modulating the functions of ER-α36 in a cell comprising exposing a cell expressing ER-α36 to the compounds of Formula (I) are provided. The cells may express ER-α36 endogenously or exogenously through genetic engineering. In one embodiment, the cells express ER-α36 endogenously. In a preferred embodiment, the cells are cancer cells that express ER-α36 endogenously. Examples of cancer cells that express ER-α36 are breast cancer cells, leukemia cells, lung cancer cells, myeloma cells, prostate cancer cells, ovarian cancer cells, colon cancer cells and stomach cancer cells. In a further preferred embodiment, the cells expressing ER-α36 are breast cancer cells that express ER-α36 endogenously. Examples of breast cancer cells expressing ER-α36 are MCF7 and MDA-MB-231 cells. The expression of the endogenous ER-α36, may be increased or decreased through treatment with one or more agents. Examples of such agents are serum, E2β (17β-estradiol), Tamoxifen and ICI 182,780.

In another embodiment, the cells are altered by genetic engineering to express exogenous ER-α36. Cells expressing exogenous ER-α36 may be prepared by genetic engineering methods known to one of ordinary skill in the art (See Sambrook et al., Molecular Cloning, A Laboratory Manual (2d Ed. 1989) (Cold Spring Harbor Laboratory)). Briefly, an exogenous ER-α36 gene is prepared and inserted into an expression vector, which is transfected into a host cell, which is then grown in a culture solution suitable for expressing the exogenous ER-α36. An example of the gene sequence of human ER-α36 is disclosed in Wang et al., *Biochem. Biophys. Res. Commun.* 336, 1023-1027 (2005) (GenBank Accession No. BX640939). The cells expressing exogenous ER-α36 may or may not express endogenous ER-α36. The expression levels of endogenous or exogenous ER-α36 in the cells may be increased or decreased by treatment with one or more other agents. Examples of such agents are serum, E2β (17β-estradiol), Tamoxifen and ICI 182,780.

The cells expressing ER-α36 may or may not express other estrogen receptors such as ER-α66, ER-α46 and ER-β.

In certain embodiments, methods of preventing and/or treating a disease related to ER-α36 in a subject comprising administering to the subject a pharmaceutical composition comprising the compounds of Formula (I) are provided. Examples of diseases related to ER-α36 include without limitation bone loss, bone fractures, osteoporosis, metastatic bone disease, Paget's disease, periodontal disease, cartilage degeneration, endometriosis, uterine fibroid disease, hot flashes, increased levels of LDL cholesterol, cardiovascular disease, impairment of cognitive functioning, cerebral degenerative disorders, restenosis, gynecomastia, vascular smooth muscle cell proliferation, obesity, incontinence, anxiety, depression resulting from an estrogen deficiency, perimenopausal depression, post-partum depression, premenstrual syndrome, manic depression, anxiety, dementia, obsessive compulsive behavior, attention deficit disorder, sleep disorders, irritability, impulsivity, immune deficiency, auto immune diseases, anger management, multiple sclerosis and Parkinson's disease, inflammation, inflammatory bowel disease, respiratory diseases, sexual dysfunction, hypertension, retinal degeneration, asthma and cancers. Preferably, diseases related to ER-α36 include bone loss, bone fracture, osteoporosis, menopause, premenstrual syndrome, endometriosis, uterine disease, impotence, sexual dysfunctions, increased levels of LDL cholesterol, cardiovascular diseases, vascular smooth muscle cell proliferation, depression resulting from an estrogen deficiency, perimenopausal depression, post-partum depression, immune deficiency, auto immune diseases, inflammation, asthma and cancers. More preferably, diseases related to ER-α36 include bone loss, osteoporosis, impotence, cardiovascular diseases, immune deficiency, inflammation, asthma and cancers. The subject may be a mammal such as a dog, cat, cow, sheep, horse, or human, preferably a human. The required therapeutic amount for the method will vary according to the specific diseases and is readily ascertainable by one of ordinary skill in the art having benefit of the instant disclosure.

In certain embodiments, methods of inducing cell death comprising exposing a cell to an effective amount of the compounds of Formula (I) are provided. Furthermore, certain embodiments of the invention provide methods of inhibiting cell proliferation comprising exposing a cell to an effective amount of the compounds of Formula (I). The cells may have normal or abnormal growth. The abnormal cell growth may be benign or malignant. In one embodiment, the cells are cancer cells. In a preferred embodiment the cancer is anal cancer, bile duct cancer, bladder cancer, bone cancer, bowel cancer (colon cancer, rectal cancer), brain cancer, breast cancer, carcinoid cancer, cervix cancer, endocrine cancer, endometrial cancer, eye cancer, gall bladder cancer, head and neck cancer, Kaposi's sarcoma cancer, kidney cancer, larynx cancer, leukemia, liver cancer, lung cancer, lymphoma, melanoma, mesothelioma, myeloma, neuroendocrine cancer, oesophagus cancer, ovary cancer, pancreas cancer, penis cancer, prostate cancer, skin cancer, soft tissue sarcomas cancer, spinal cord cancer, stomach cancer, testes cancer, thyroid cancer, vagina cancer, vulva cancer, or uterus cancer. In a further preferred embodiment, the cancer is breast cancer, cervix cancer, colon cancer, endometrial cancer, leukemia, liver cancer, lung cancer, myeloma, ovary cancer, prostate cancer, stomach cancer, or uterus cancer. In an even further preferred embodiment, the cancer is breast cancer, cervix cancer, endometrial cancer, lung cancer, uterus cancer or prostate cancer. In certain embodiments, the cells may express estrogen receptors, in particular, ER-α36, endogenously or exogenously. In a preferred embodiment, the cells express ER-α36 endogenously.

The effective amount of the compounds of Formula (I) for inducing cell death and/or inhibiting cell proliferation will vary according to the specific cell types and treatment conditions. It is readily ascertainable by one of ordinary skill in the art having benefit of the instant disclosure. In one embodiment, the effective amount of the compounds of Formula (I) that the cell is exposed to is a concentration of at least about 5 μM. In another embodiment, the concentration of the compounds of Formula (I) that the cell is exposed to is within the range of about 5 μM to 100 μM. Preferably, the effective amount is a concentration of the compounds within the range of about 5 μM to 50 μM or about 5 μM to 30 μM or about 5 μM to 25 μM or about 5 μM to 20 μM or about 5 μM to 10 μM.

In certain embodiments, methods of preventing and/or treating a disease involving abnormal cell proliferation in a subject comprising administering to the subject a therapeutically effective amount of a pharmaceutical composition comprising the compounds of Formula (I) are provided.

The abnormal cell proliferation may be benign cell growth or cancerous. In one embodiment, the disease involving abnormal cell proliferation is cancer. In a preferred embodiment the cancer is anal cancer, bile duct cancer, bladder cancer, bone cancer, bowel cancer (colon cancer, rectal cancer), brain cancer, breast cancer, carcinoid cancer, cervix cancer, endocrine cancer, endometrial cancer, eye cancer, gall bladder cancer, head and neck cancer, Kaposi's sarcoma cancer, kidney cancer, larynx cancer, leukemia cancer, liver cancer, lung cancer, lymphoma cancer, melanoma cancer, mesothelioma cancer, myeloma cancer, neuroendocrine cancer, oesophagus cancer, ovary cancer, pancreas cancer, penis cancer, prostate cancer, skin cancer, soft tissue sarcomas cancer, spinal cord cancer, stomach cancer, testes cancer, thyroid cancer, vagina cancer, vulva cancer, or uterus cancer. In a further preferred embodiment, the cancer is breast cancer, cervix cancer, colon cancer, endometrial cancer, leukemia, liver cancer, lung cancer, myeloma, ovary cancer, prostate cancer, stomach cancer, or uterus cancer. In an even further preferred embodiment, the cancer is breast cancer, cervix cancer, endometrial cancer, lung cancer, uterus cancer or prostate cancer.

In certain embodiments, methods of preventing and/or treating asthma and other respiratory diseases in a subject comprising administering to the subject a therapeutically effective amount of a pharmaceutical composition comprising the compounds of Formula (I) are provided. Asthma refers to inflammatory disorders of the airways with reversible airflow obstruction. Other respiratory diseases may include disorders of the respiratory tracts and lung such as bronchitis, cystic fibrosis, emphysema, pneumonia, rhinitis and sinusitis.

The subject is preferably a mammal. In one embodiment, the mammal is a dog, cat, cow, sheep, horse, or human. In a preferred embodiment, the mammal is a human.

The compounds of Formula (I) may be administered to a subject by any method that enables delivery of the compounds to the site of action. These methods include, without limitation, oral, buccal, sublingual, ocular, topical (e.g., transdermal), parenteral (e.g., intravenous, intramuscular, or subcutaneous, intravascular or infusion), rectal, intracisternal, intravaginal, intraperitoneal, intravesical, or nasal methods.

The compounds of Formula (I) may be administered to a subject at dosage levels in the range of from about 0.1 mg to about 3,000 mg per day, preferably from about 0.1 mg to about 1,000 mg per day, or from about 1 mg to about 500 mg per day, or from about 1 mg to about 300 mg per day, or from about 10 mg to about 300 mg per day, or from about 10 mg to about 200 mg per day, or from about 20 mg to about 200 mg per day, or from about 30 mg to about 200 mg per day, or from about 40 mg to about 200 mg per day, or from about 50 mg to about 200 mg per day, or from about 50 mg to about 100 mg per day. For a normal adult human having a body mass of about 70 kg, a dosage in the range of from about 0.01 mg to about 100 mg per kg body mass is typically sufficient, and preferably from about 0.1 mg to about 100 mg per kg, or from about 0.5 mg to about 100 mg per kg, or from about 1 mg per kg to about 100 mg per kg, or from about 1 mg per kg to about 75 mg per kg, or from about 1 mg per kg to about 50 mg per kg, or from about 1 mg per kg to about 25 mg per kg, or from about 1 mg per kg to about 10 mg per kg, or from about 2 mg per kg to about 5 mg per kg. However, some variability in the general dosage range may be required depending upon the age and mass of the subject being treated, the intended route of administration, the particular compound being administered, and the like. The determination of dosage ranges and optimal dosages for a particular mammalian subject is within the ability of one of ordinary skill in the art having benefit of the instant disclosure.

In certain embodiments, one or more compounds of the invention may be used in combination with one another. Optionally, the compounds of the invention may also be used in combination with any other active agents for modulating cell functions or treating diseases. If a combination of active compounds is used, they may be administered simultaneously, separately or sequentially.

In certain embodiments, the compounds of the invention may be used in combination with one or more other anticancer agents. Suitable anticancer agents include, but are not limited to, alkylating agents, nitrogen mustards, folate antagonists, purine antagonists, pyrimidine antagonists, spindle poisons, topoisomerase inhibitors, apoptosis inducing agents, angiogenesis inhibitors, podophyllotoxins, nitrosoureas, antimetabolites, protein synthesis inhibitors, kinase inhibitors, antiestrogens, cisplatin, carboplatin, interferon, asparginase, leuprolide, flutamide, megestrol, mitomycin, bleomycin, doxorubicin, irinotecan and taxol. In one embodiment, the anticancer agents are antiestrogens such as tamoxifen and ICI 182,780.

The compounds of the invention can be tested for their ability to induce cell death or inhibit cell proliferation using recombinant cells expressing exogenous ER-α36. To make the recombinant cells, an exogenous ER-α36 gene is prepared and inserted into an expression vector, then host cells that do not express or express low level of endogenous ER-α36 are transfected with the expressing vector and stably transfected host cells are selected as the recombinant cells for the testing assay. The recombinant cells are incubated with or without the compounds of the invention. The numbers of cells surviving in the assays with or without the treatment of the compounds of the invention are compared. When the number of cells surviving in the assays with the treatment of the test compound are lower (with statistical significance) than the number of cells surviving in the assays without the test compound, the test compound can induce cell death and/or inhibit cell proliferation.

The recombinant cells discussed above can also be used to test compounds of the invention for their ability to modulate ER-α36 functions. The recombinant cells expressing exogenous ER-α36 and the non-transfected host cells are treated with the test compound under the same conditions. The functions of ER-α36 of interest are observed and analyzed with methods known to one with ordinary skill in the art. Such functions include but are not limited to ER-α36's ability to stimulate its downstream signal transduction pathways such as activation of the Mitogen-Activated Protein kinase (the MAPK/ERK) pathway or the Jun NH2-terminal Kinases (JNKs) pathway.

Pharmaceutical Compositions

In certain embodiments of the methods of the present invention, a compound of Formula (I), a stereoisomer or prodrug thereof, or a pharmaceutically acceptable salt of the compound, stereoisomer, or prodrug, may be administered in the form of a pharmaceutical composition comprising a pharmaceutically acceptable carrier, vehicle, or diluent. Accordingly, a compound of Formula (I), a stereoisomer or prodrug thereof, or a pharmaceutically acceptable salt of the compound, stereoisomer, or prodrug, may be administered to a subject separately or together in any conventional dosage form, including, oral, buccal, sublingual, ocular, topical, parenteral, rectal, intracisternal, intravaginal, intraperitoneal, intravesical, local (e.g., powder, ointment, or drop), or nasal dosage forms.

Pharmaceutical compositions suitable for parenteral injection may comprise pharmaceutically acceptable sterile aqueous or nonaqueous solutions, dispersions, suspensions, or emulsions, and sterile powders for extemporaneous reconstitution into sterile injectable solutions or dispersions. Examples of suitable aqueous and nonaqueous carriers, vehicles, and diluents include water, ethanol, polyols (such as propylene glycol, polyethylene glycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

In certain embodiments, pharmaceutical compositions of the invention may further comprise adjuvants, such as preserving, wetting, emulsifying, and dispersing agents. Prevention of microorganism contamination of the instant compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions may be affected by the use of agents capable of delaying absorption, for example, aluminum monostearate and gelatin.

Solid dosage forms for oral administration can include capsules, tablets, powders, and granules. In certain embodiments of such solid dosage forms, the active compound is admixed with at least one inert conventional pharmaceutical excipient (or carrier) such as sodium citrate or dicalcium phosphate, or (a) fillers or extenders, such as for example, starches, lactose, sucrose, mannitol, or silicic acid; (b) binders, such as for example, carboxymethyl-cellulose, alginates, gelatin, polyvinylpyrrolidone, sucrose, or acacia; (c) humectants, such as for example, glycerol; (d) disintegrating agents, such as for example, agar-agar, calcium carbonate, potato or tapioca starch, alginic acid certain complex silicates, or sodium carbonate; (e) solution retarders, such as for example, paraffin; (f) absorption accelerators, such as for example, quaternary ammonium compounds; (g) wetting agents, such as for example, cetyl alcohol or glycerol monostearate; (h) adsorbents, such as for example, kaolin or bentonite; and/or (i) lubricants, such as for example, talc, calcium stearate, magnesium stearate, solid polyethylene glycols, sodium lauryl sulfate, or mixtures thereof. In the case of capsules and tablets, the dosage forms may further comprise buffering agents.

In certain embodiments, solid dosage forms may be formulated as modified release and pulsatile release dosage forms containing excipients such as those detailed above for immediate release dosage forms together with additional excipients that act as release rate modifiers, these being coated on and/or included in the body of the device. Release rate modifiers include, but are not limited to, hydroxypropylmethyl cellulose, methyl cellulose, sodium carboxymethylcellulose, ethyl cellulose, cellulose acetate, polyethylene oxide, xanthan gum, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients.

In certain embodiments, the pharmaceutical compositions of the invention may further comprise fast dispersing or dissolving dosage formulations (FDDFs) containing the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e., where the drug substance is insoluble, a fast dispersing dosage form may be prepared, and where the drug substance is soluble, a fast dissolving dosage form may be prepared.

Solid compositions of a similar type may also be employed as fillers in soft or hard filled gelatin capsules using such excipients as lactose or milk sugar, as well as high molecular weight polyethylene glycols, and the like.

In certain embodiments, solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound(s) in a delayed, sustained, or controlled manner. Examples of embedding compositions that can be employed are polymeric substances and waxes. The active compound(s) can also be in micro-encapsulated form, if appropriate, with one or more of the above-mentioned excipients.

In certain embodiments, liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and/or emulsifiers, as for example, ethyl alcohol, isopropyl alcohol, ethyl carbonate, benzyl benzoate, propylene glycol, 1,3-butylene glycol, oils, in particular, cottonseed oil, groundnut oil, corn germ oil, olive oil, castor oil, or sesame seed oil, glycerol, tetrahydrofurfuryl alcohol, polyethylene glycols or fatty acid esters of sorbitan, or mixtures of these substances, and the like.

Besides such inert diluents, the pharmaceutical composition can also include adjuvants, such as wetting agents, emulsifying and suspending agents, sweetening, flavoring, and perfuming agents. The pharmaceutical composition may further include suspending agents, such as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

In certain embodiments, pharmaceutical compositions of the present invention may also be configured for treatments in veterinary use, where a compound of the present invention, or a veterinarily acceptable salt thereof, or veterinarily acceptable solvate or pro-drug thereof, is administered as a suitably acceptable formulation in accordance with normal veterinary practice and the veterinary practitioner will determine the dosing regimen and route of administration which will be most appropriate for a particular animal.

If a combination of active agents is administered, then they may be administered simultaneously, separately or sequentially.

Compounds of Formula (I) may be prepared by following prior arts as well as by other conventional organic preparative methods (Yu, L. J.; Hu, Y. Z. *China Pharm. J* 2005, 40, 1029 and references cited herein. Nikaido, T.; Ohmoto, T.; Kinoshita, T.; Sankawa, U.; Monache, F. D.; Botta, B.; Tomimori, T.; Miyaichi, Y.; Shirataki, Y.; Yokoe, I.; Komatsu, M. *Chem. Pharm. Bull.* 1989, 37, 1392 and references cited herein).

EXAMPLES

The following Examples are further illustrations of the present invention, but are not to be construed to limit the scope of the present invention.

Example 1

Expression of ER-α Variants in Human Breast Cancer Specimens

A membrane pre-blotted with human breast cancer tissues was purchased from ProSci Incorporated (Poway, Calif.). The membrane was probed with an anti-ER-α36 antibody that specifically recognizes ER-α36 and an HRP-conjugated secondary antibody, and visualized with enhanced chemiluminescence (ECL) detection reagents (Amersham Pharmacia Biotech). The same membrane was then stripped and detected with an anti-estrogen receptor-α antibody H222 (Novocastra Laboratories Ltd, UK) that recognizes all three subtypes of ER-1, ER-α66, ER-α46 and ER-α36. FIG. 1 shows that ER-α66, ER-α46 and ER-α36 are not expressed in normal breast tissue (Lane 1) but expressed in one specimen of infiltrating ductal carcinoma (Lane 2), one specimen of infiltrating lobular carcinoma (Lane 5), and non-invasive ductal carcinoma (Lane 7). In addition, ER-α36 is expressed in invasive ductal carcinoma (Lane 4) and another specimen of infiltrating lobular carcinoma (Lane 6). Lanes 2 and 3 had infiltrating ductal carcinoma from two different patients, respectively. Lanes 5 and 6 had infiltrating lobular carcinoma from two different patients, respectively. This result indicates that ER-α36 is not expressed in normal breast tissue but expressed in ER-negative breast cancer samples that do not express ER-α66 and ER-α46.

Example 2

ER-α36 is Expressed in the ER-negative Breast Cancer Cell Line, MDA-MB-231

Figure 2:
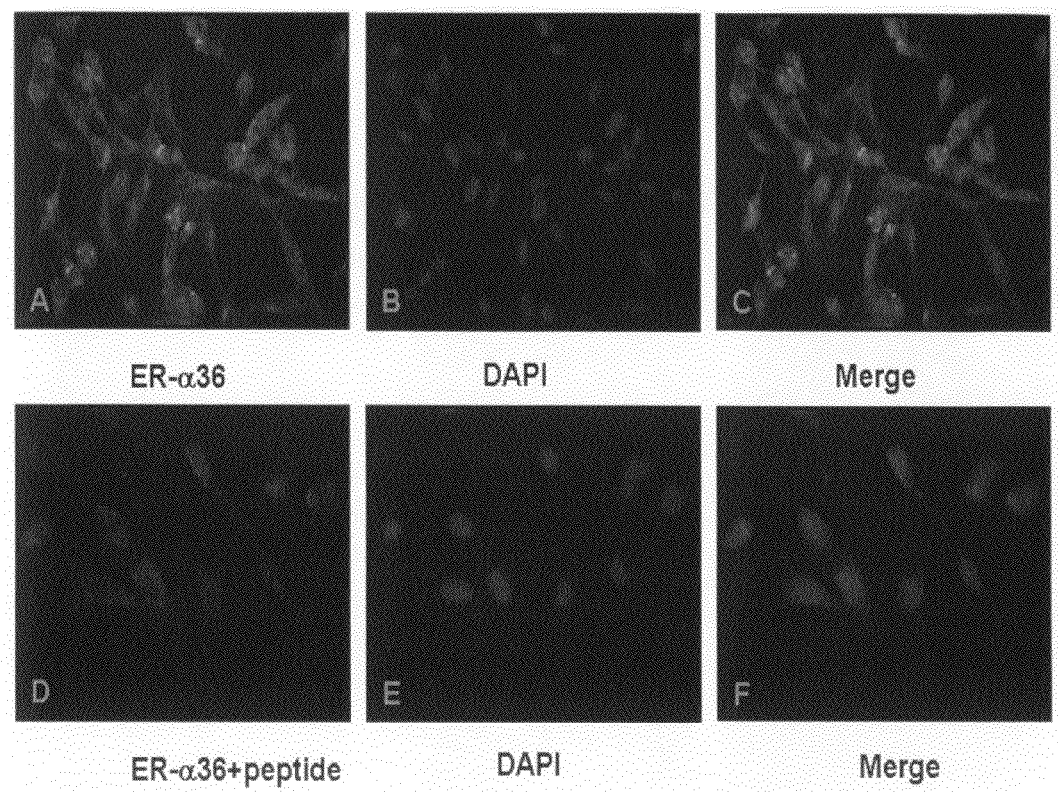
FIG. 2 (upper panel) shows the immunofluorescence staining result of MDA-MB-231 cells, an ER-negative breast cancer cell line that lacks ER-α66 and ER-α46, stained with an antibody that specifically binds to ER-α36 (shown in the figure labeled with "ER-α36": positive staining shown in green). Cell nucleus was also stained with 4,6-Diamidine-2-Phenylindole (shown in the lane labeled with "DAPI": positive staining shown in blue). Merged staining signals were shown in lane labeled with "Merge". Negative staining was observed when the antibody was pre-incubated with immunogen peptides that bind to the antibody (lower panel).

The MDA-MB-231 cell line is well-known for lacking ER-α66 and ER-α46 (Relevance of breast cancer cell lines as models for breast tumours: an update. Marc Lacroix, Guy Leclercq, Breast Cancer Research and Treatment 83: 249-289 (2004)). MDA-MB-231 cells were obtained from American Type Cell Culture (ATCC). MDA-MB-231 cells were grown on 8-well BIOCOAT chamber slides (BD Science Discovery Labware) in a 5% $CO_2$ atmosphere in Dulbecco's Modified Eagle's Medium (DMEM) and 10% fetal calf serum at 37° C. for 12 hours. Then the cells were washed twice with sterile Phosphate Buffered Saline (PBS) and fixed with 4% paraformaldehyde in PBS (pH 7.4) for 30 minutes at room temperature. After that, the cells were washed with PBS, permeabilized with 0.5% (v/v) Triton X-100 for 10 minutes. The cells were then washed with PBS again, and blocked with 3% serum in PBS at room temperature for 1 hour. The slides were incubated with an ER-α36 specific antibody or the same antibody preincubated with immunogen peptides that bind to the antibody for 30 minutes at room temperature for 1 hour and washed three times with PBS containing 0.5% Triton X-100 (PBST), then incubated with a fluorescein isothiocyanate (FITC)-conjugated secondary antibody. Finally, the slides were washed three times with PBST, one time with PBS, then coated with anti-fade medium (Molecular Probes, Eugene, Oreg.) and examined under a Nikon E600 Microscope and images were captured by the MRC-1024 confocal imaging system (Bio-Rad). FIG. 2 (upper panel) shows that MDA-MB-231 cells were stained positive by an anti-ER-α36 antibody. Incubation with the same antibody preincubated with the immunogen peptides did not show any staining (FIG. 2, lower panel), indicating the specificity of the antibody.

Example 3

Icaritin Induces Cell Death in ER-negative Breast Cancer MDA-MB-231 Cells

Figure 3:
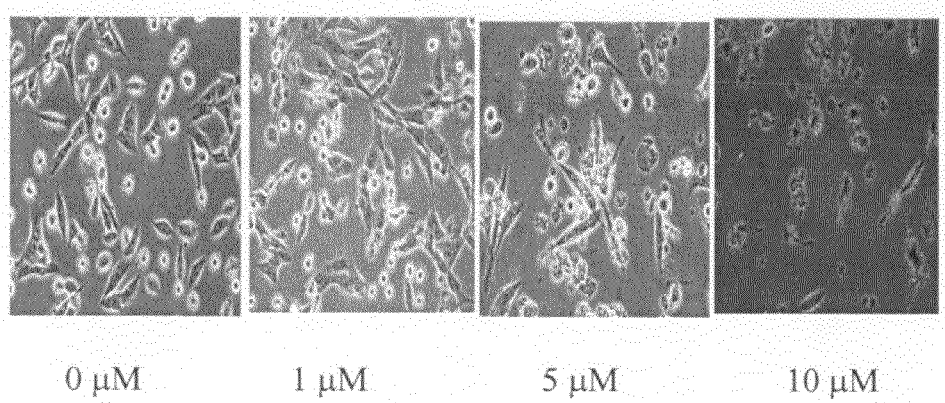
FIG. 3 is microscope photo of MDA-MB-231 cells after treatment with Icaritin at the concentrations of zero, 1 µM, 5 µM and 10 µM for a week.

MDA-MB-231 cells were maintained at 37° C. in a 5% $CO_2$ atmosphere in DMEM and 10% fetal calf serum. The cells were plated at a density of $1 \times 10^5$ cells per 60-mm dish. MDA-MB-231 cells were treated with Icaritin dissolved in DMSO at the concentrations of zero, 1 μM, 5 μM and 10 μM for a week. Icaritin was purchased from Shanghai Yousi Biotechnology Co., Ltd. Treated cells were examined under a Nikon TS100 inverted microscope and photographed for morphological changes. FIG. 3 shows that when treated with 10 μM Icaritin, the cells exhibited features characteristic of apoptotic cells and the number of surviving cells was dramatically reduced.

Figure 4:
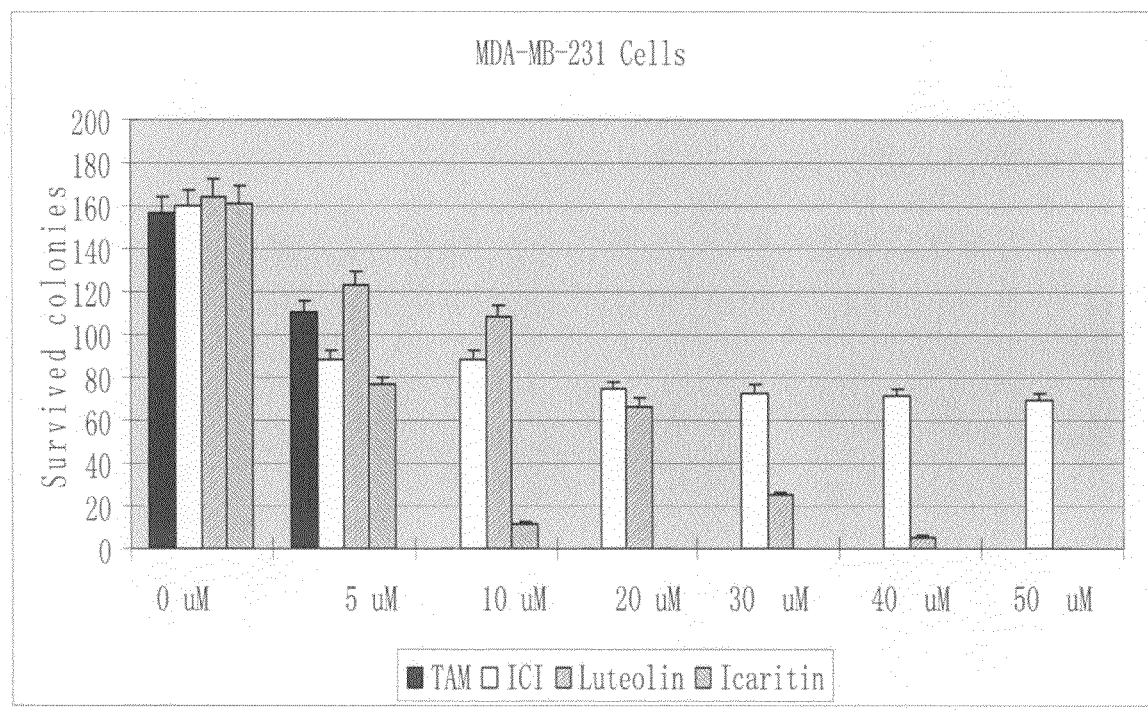
FIG. 4 is a histogram graph of the numbers of colonies of MDA-MB-231 cells after treatment with Tamoxifen (TAM), ICI 182,780 (ICI), Luteolin and Icaritin at concentrations of zero, 5 µM, 10 µM, 20 µM, 30 µM, 40 µM and 50 µM for 10 days.

In addition, MDA-MB-231 cells were treated with Tamoxifen, ICI 182,780, Luteolin, Icaritin at concentrations of zero, 5 μM, 10 μM, 20 μM, 30 μM, 40 μM and 50 μM to test the effect of these compounds on MDA-MB-231 cell growth. Tamoxifen and Luteolin were purchased from Sigma, St. Louis, Mo.; ICI 182,780 was purchased from Tocris Bioscience, Ellisville, Mo. These compounds were dissolved in DMSO. The MDA-MB-231 cells were sub-seeded at 500 cells per 60 mm dish and incubated with the different compounds separately for 10 days. Cells that survived the compound treatment formed colonies. The cell colonies were stained with 0.5 ml of 0.02% crystal violet, 20% ethanol, 0.74% formaldehyde, and 80% $H_2O$ for 10 minutes. The stained colonies were counted under light microscope. FIG. 4 shows that the numbers of colonies of MDA-MB-231 cells were decreased with the treatment of 5 μM Icaritin, Luteolin, Tamoxifen or ICI 182,780. The numbers of MDA-MB-231 colonies were further reduced to near zero with the treatment of 10 μM Icaritin or Tamoxifen. When treated with Luteolin, the number of MDA-MB-231 colonies dropped to near zero at the concentration of 40 μM. However, when treated with ICI 182,780, the number of colonies remained at a high level at a concentration of 50 μM.

Example 4

Icaritin Induces Cell Death in ER-positive Breast Cancer MCF7 Cells

Figure 5A:
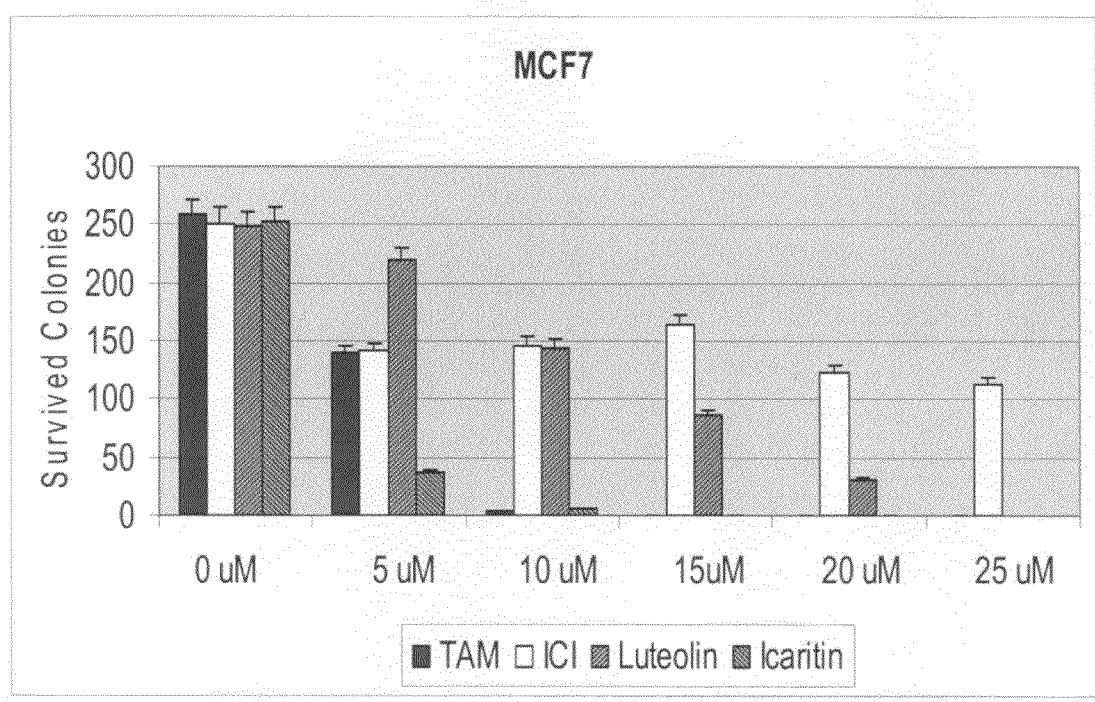
FIG. 5a shows a histogram graph of the numbers of colonies of MCF7 cells after treatment with Tamoxifen (TAM), ICI 182,780 (ICI), Luteolin and Icaritin at the concentration of zero, 5 µM, 10 µM, 15 µM, 20 µM and 25 µM for 10 days.

MCF7 cell line is a breast cancer cell line that strongly expresses ER-α66, ER-α46 and ER-α36 (Relevance of breast cancer cell lines as models for breast tumours: an update. Marc Lacroix, Guy Leclercq, Breast Cancer Research and Treatment (2004) 83, 249-289; Wang et al., Proc. Natl. Acad. Sci. U.S.A. 103:9063-9068 (2006)). MCF7 cells obtained from ATCC were maintained in DMEM/F12 medium (Invitrogen) supplemented with 10% fetal calf serum at 37° C. in a 5% $CO_2$ atmosphere. The MCF7 cells were treated with Tamoxifen, ICI 182,780, Luteolin and Icaritin at concentrations from zero to 25 μM to test the effect of these compounds on MCF7 cell growth for 10 days. The experiments were conducted in the same way as the experiment for FIG. 4 in Example 3 above. FIG. 5a shows that Tamoxifen, Luteolin and Icaritin significantly reduced the number of colonies of MCF7 cells as their concentration rose. ICI 182,780 induced only a limited decrease of cell colonies even at 25 μM.

Figure 5B:
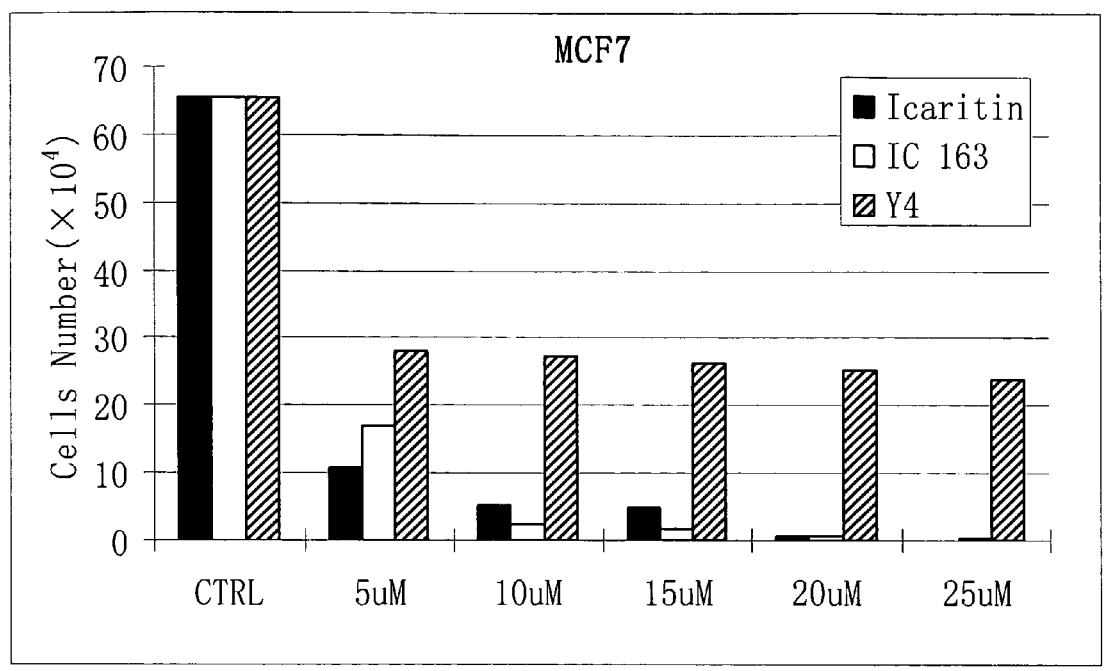
FIG. 5b shows a histogram graph of the numbers of surviving MCF7 cells after treatment with Icaritin, IC 163 and Y4 at the concentrations of zero, 5 µM, 10 µM, 15 µM, 20 µM and 25 µM for two weeks.

In another experiment, MCF7 cells were treated with Icaritin, IC 163 and Y4, respectively, to compare the effect of these compounds on MCF7 cell growth. IC 163 and Y4 were purchased from Shanghai Yousi Biotechnology Co., Ltd. The MCF7 cells were plated at a density of 1×10$^5$ cells per 100-mm dish and treated with each compound at concentrations from zero to 25 μM for two weeks. The numbers of survived cells were counted using a hemocytometer. Five dishes of cells were counted for each concentration point. FIG. 5b shows that each compound significantly reduced the numbers of surviving MCF7 cells at the concentration of 5 μM and up.

Example 5

Icaritin Induces Cell Death in MCF7 Cells Over-Expressing ER-α36 and Tamoxifen Resistant MCF7 Cells MCF7 cells over-expressing ER-α36 were made by stably transfecting MCF cells with an ER-α36 expression vector. The ER-α36 expression vector was constructed by cloning a 1.1-kb cDNA fragment of ER-α36 from pBluescript plasmid into a mammalian expression vector pCB6+ as described before (Wang et al., 2005, BBRC, 336:1023-1027). The constructed ER-α36 expression vector contains the cytomegalovirus (CMV) early promoter. MCF7 cells were transfected with the ER-α36 expression vector using the FuGene6 transfection reagent (Roche Molecular Biochemicals). Forty-eight hours after transfection, the cells were re-plated and selected with 500 μg/ml of G418 (Invitrogen) for about two weeks until colonies appeared. The clones were then pooled and cultured to confirm the expression of ER-α36 by Western blot analysis.

Tamoxifen-resistant MCF7 cells were generated by incubating MCF7 cells in medium containing 5 μM Tamoxifen for three months. MCF7 cells that were still alive after three months were pooled and further cultured as Tamoxifen-resistant MCF7 cells. Western blot analysis revealed that these cells highly express ER-α36 (data not shown).

Figure 6:
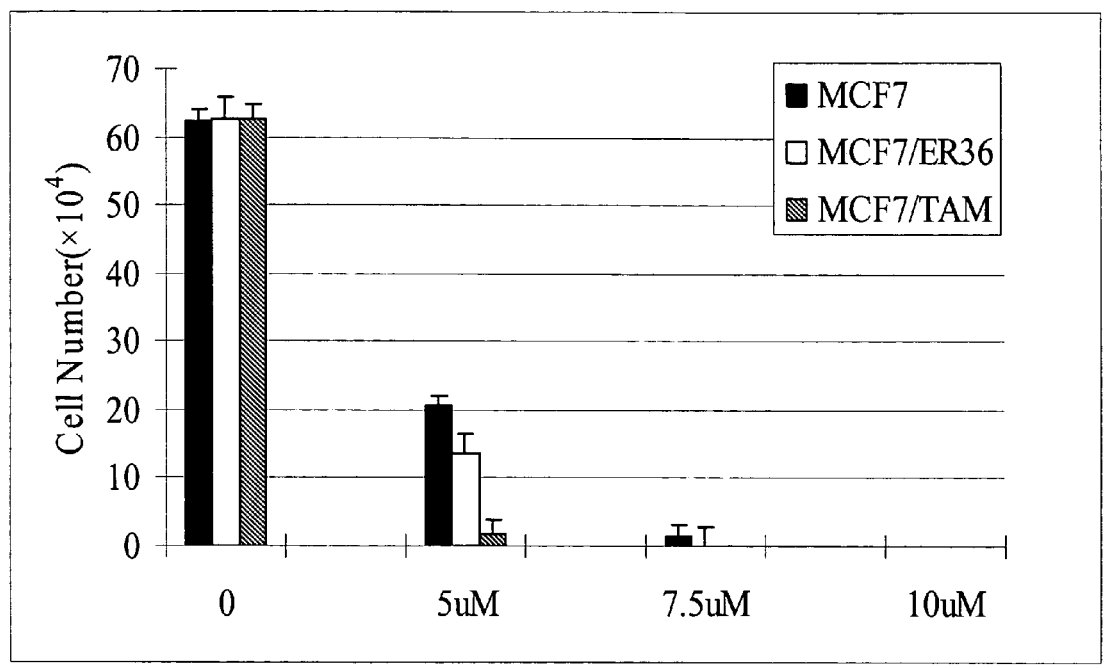
FIG. 6 is a histogram graph showing the numbers of surviving cells after MCF7 cells, MCF7 cells over-expressing ER-α36 (MCF7/ER36) and Tamoxifen resistant MCF7 cells (MCF7/TAM) were treated with Icaritin at zero, 5 µM, 7.5 µM and 10 µM for two weeks.

The cell lines were maintained in DMEM/F12 medium supplemented with 10% fetal calf serum at 37° C. in a 5% CO$_2$ atmosphere. Cells were plated at a density of 1×05 cells per 100-mm dish and treated with Icaritin at concentrations of zero to 10 μM for two weeks. The numbers of survived cells after two weeks were counted. Five dishes of cells were counted for each concentration point. FIG. 6 shows that at 5 μM of Icaritin, growth of all three types of cells was significantly inhibited, and the inhibition was stronger in MCF7 cell over-expressing ER-α36 and TAM-resistant MCF7 cells than in MCF7 cells. At 10 μM, Icaritin reduced the numbers of all three types of cells to near zero.

Example 6

Normal Mammary Epithelial Cell Growth is Not Affected by Icaritin

Figure 7:
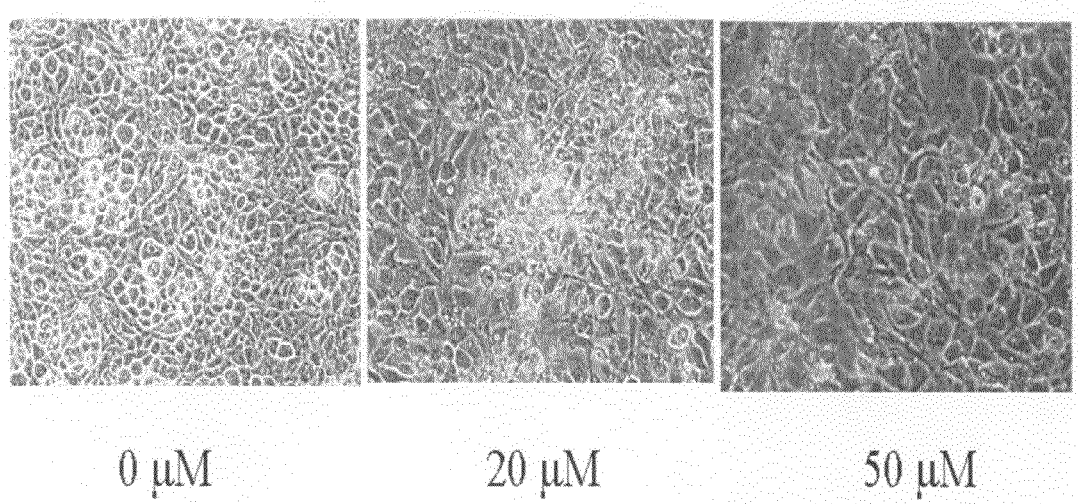
FIG. 7 shows microscope photos of normal mammary epithelial MCF10A cells after treatment with Icaritin at concentrations of zero, 20 µM and 50 µM for two weeks.

Normal mammary epithelial cells MCF10A were obtained from Karmanos Cancer Institute at Detroit, Mich. These MCF10A cells do not express any of the ER isoforms, ER-α36, ER-α46 and ER-α66. The MCF10A cells were maintained at 37° C. in a 10% CO$_2$ atmosphere in DMEM/F12 medium supplemented with 5% horse serum, L-Glutamine (2 mM), penicillin (100 U/ml), streptomycin (100 μg/ml), hydrocortisone (0.5 μg/ml), insulin (10 μg/ml), EGF (2 ng/ml), cholera toxin (0.1 μg/ml) and fungizone (0.5 μg/ml). The MCF10A cells were plated at a density of 1×10$^5$ cells per 100-mm dish containing zero, 20 μM and 50 μM of Icaritin, respectively, for two weeks. Then the cells were examined under a Nikon TS100 inverted microscope and photographed for morphological changes. FIG. 7 shows that the morphology of MCF10A cells was not changed by treatment with Icaritin at a concentration as high as 50 μM.

Example 7

Regulation of the Expression of ER-1 Variants by Different Agents

MCF7 cells were treated with different agents and the expression of ER-α66, ER-α46 and ER-α36 was analyzed by Western blot analysis.

Figure 8:
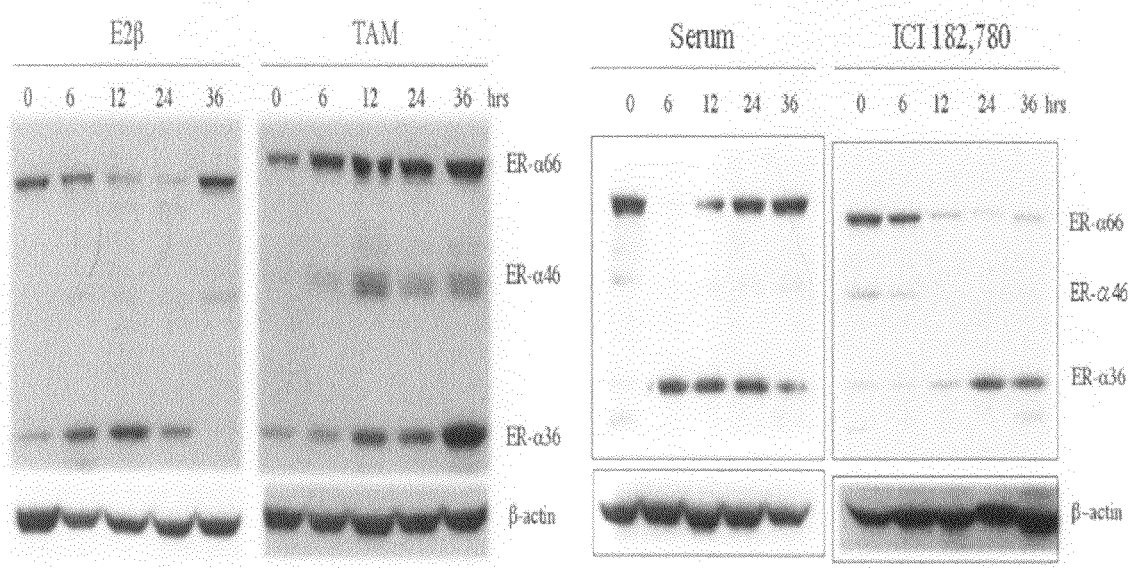
FIG. 8 shows Western blot results depicting the expression patterns of ER-α66, ER-α46 and ER-α36 in MCF7 cells after treatment with 17β-estradiol (E2β), Tamoxifen (TAM), serum and ICI 182,780 for up to 36 hours.

Serum-starved MCF7 cells were treated with 10 μM of 17β-estradiol (E2β), Tamoxifen or ICI 182,780 or serum (20%) for different time period. The treated cells were washed with PBS and lysed with lysis buffer (50 mM Tris-HCl pH8.0, 150 mM NaCl, 0.25 mM EDTA pH8.0, 0.1% SDS, 1% Triton X-100, 50 mM NaF, and protease inhibitor cocktail from Sigma). The lysates were boiled for 5 minutes in SDS gel loading buffer (25 mM Tris-Cl pH 6.8; 10% SDS; 2% Glycerol; 20% β-mercaptoethanol; 0.01% Bromophenol blue) and separated on a 10% SDS-PAGE gel. After electrophoresis, the proteins were transferred to a PVDF membrane (Bio Rad Laboratories, Hercules, Calif.). The membranes were probed with the anti-estrogen receptor-α antibody H222. Then the membranes were incubated with an HRP-conjugated secondary antibody and visualized with ECL detection reagents. FIG. 8 shows that E2β treatment dramatically reduced both ER-α66 and ER-α46 expressions but induced ER-α36 expression. Serum treatment had a similar effect. Tamoxifen, however, stabilized expression levels of ER-α66 and ER-α46, and also increased ER-α36 expression levels. ICI 182,780 dramatically reduced levels of ER-α66 and ER-α46, and at the same time increased levels of ER-α36 expression.

Figure 9:
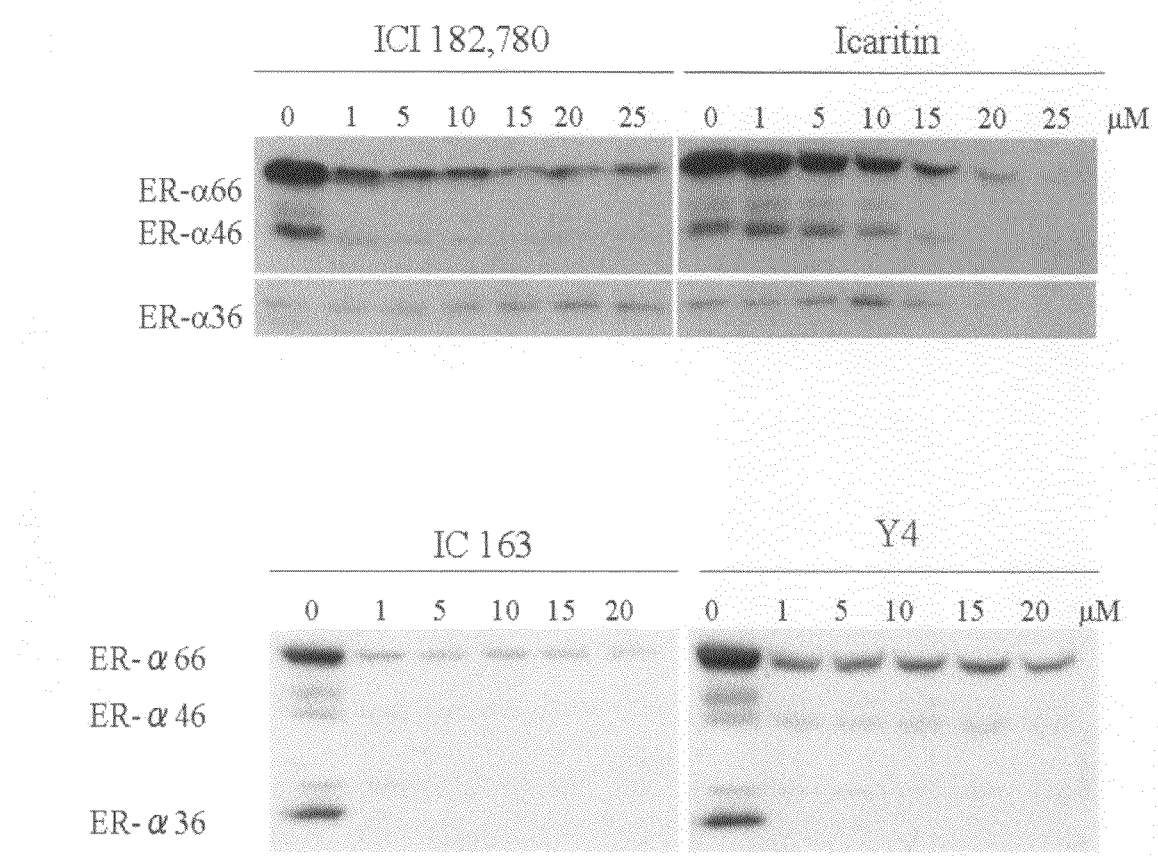
FIG. 9 shows Western blot results depicting expression of ER-α66, ER-α46 and ER-α36 in MCF7 cells after treatment for 12 hours with zero to 25 µM ICI 182,780, Icaritin, IC 163 and Y4.

In addition, MCF7 cells were treated with different concentrations of IC$_1$-182,780, Icaritin, IC 163 or Y4 for 12 hours. The expression of ER-α66, ER-α46 and ER-α36 was analyzed by Western blot analysis as described above. FIG. 9 shows that ICI 182,780 treatment reduced ER-α66 and ER-α46 expression but increased ER-α36 expression as its concentration increases. However, at higher concentration, Icaritin significantly reduced the expression levels of all three isoforms, ER-α66, ER-α46 and ER-α36. IC163 or Y4 treatment also greatly reduced the expression of all three ER isoforms.

Example 8

Icaritin Induces Cell Death in Lung and Prostate Cancer Cells

Figure 10:
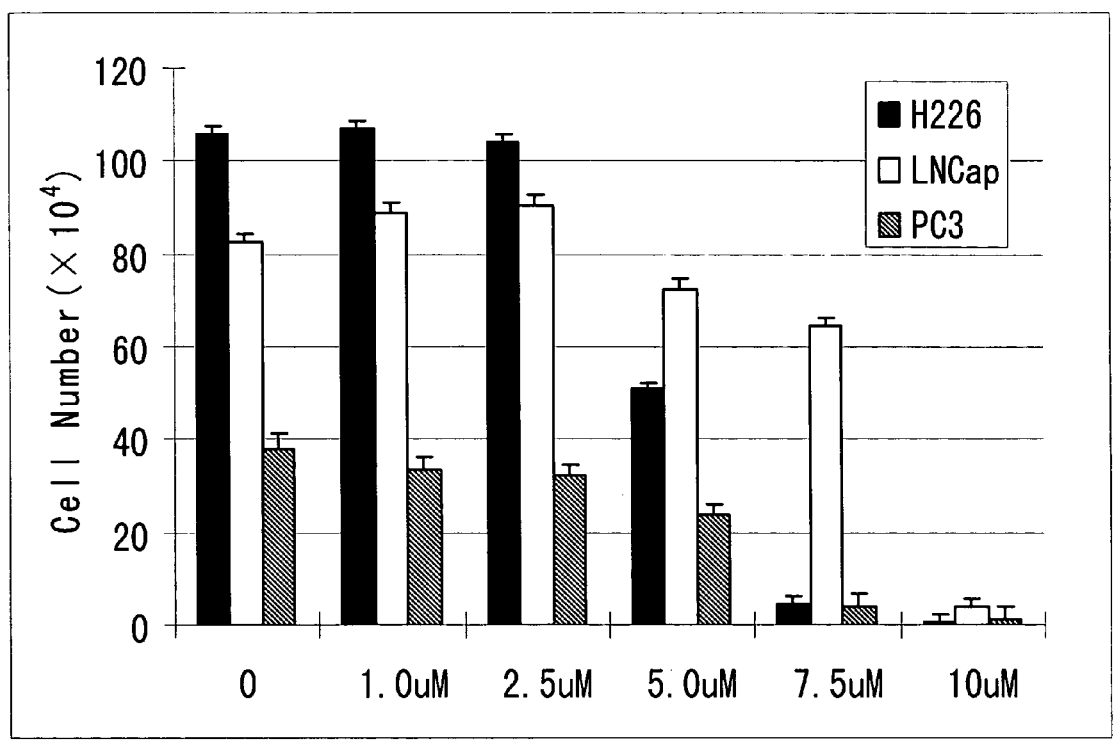
FIG. 10 is a histogram graph showing the numbers of surviving cells after H226 Lung Cancer Cells (a lung epithelial cancer cell line that expresses a moderate level of ER-α36), LNCap cells (a prostate cancer cell line that expresses a moderate level of ER-α36), and PC3 cells (a prostate cancer cell line that expresses a high level of ER-α36) were treated with Icaritin at concentrations from zero to 10 µM.

H226 Lung Cancer Cells, LnCap cells and PC3 cells were each plated at a density of 1×10$^4$ cells per 30-mm dish. The cells were treated with Icaritin for two weeks. The numbers of surviving cells were counted using a hemocytometer. Icaritin treatment was tested at the concentration of zero, 1.0 μM, 2.5 μM, 5.0 μM, 7.5 μM and 10 μM, respectively. Five dishes of cells were counted for each concentration point. FIG. 10 shows that the numbers of cells of all cell lines were decreased with the treatment of 5 μM Icaritin. At 10 μM, the numbers of cells from all cell lines were further reduced. Thus, Icaritin also induces cell death in lung and prostate cancer cells.

Example 9

Icaritin Inhibits Growth of ER-Positive and ER-Negative Breast Cancer Xenografts in Nude Mice Icaritin for administration to animals was prepared in corn oil. To make Icaritin in corn oil, 5 ml of corn oil was put in a scintillation vial and heated at 42° C. for 30 minutes. 100 mg of Icaritin was added into the pre-heated 5 ml corn oil at the final concentration of 20 mg/ml. The vial was wrapped with aluminium foil and placed on a rocker at 37° C. for several hours. The Icaritin solution was stored at 4° C. and ready to be used for animal administration. The Icaritin solution was administered to mice using the gavage technique. For gavaging, we used Animal Feeding Needles (Popper; cat No. 9921, size: 20GX1.1/2).

Figure 11:
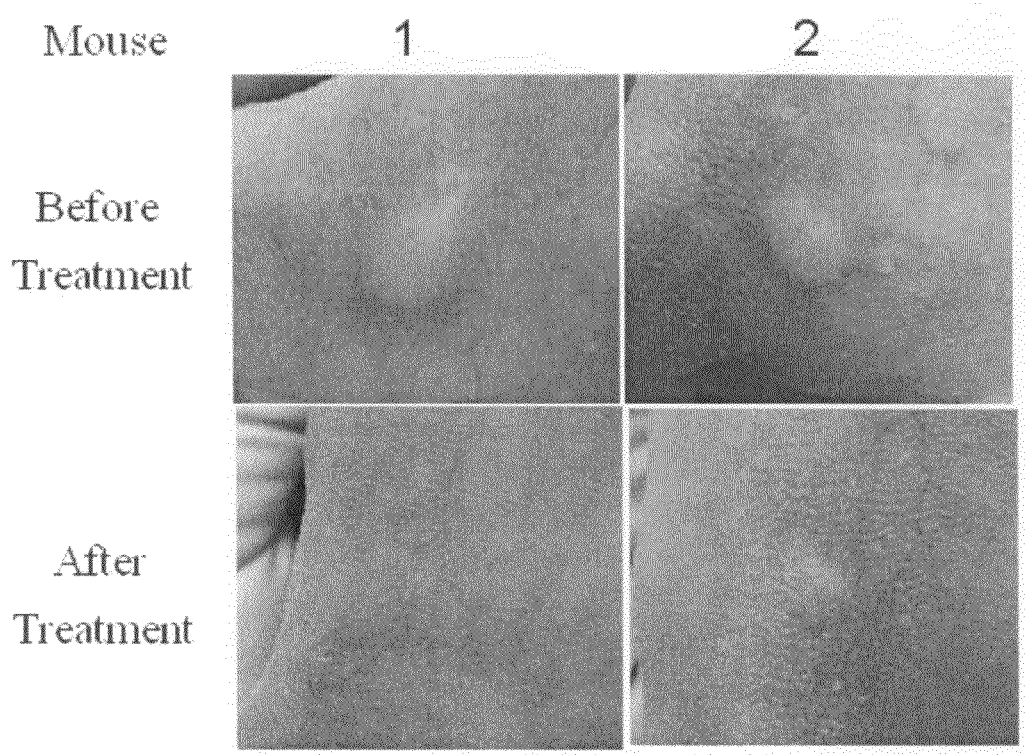
FIG. 11 shows pictures depicting the size reduction of breast cancer MDA-MB-231 cell xenografts in nude mice after treatment with Icaritin at 5 mg per mouse, once every other day for 30 days. Two representative tumors from two different mice before and after treatment were shown.
Figure 12:
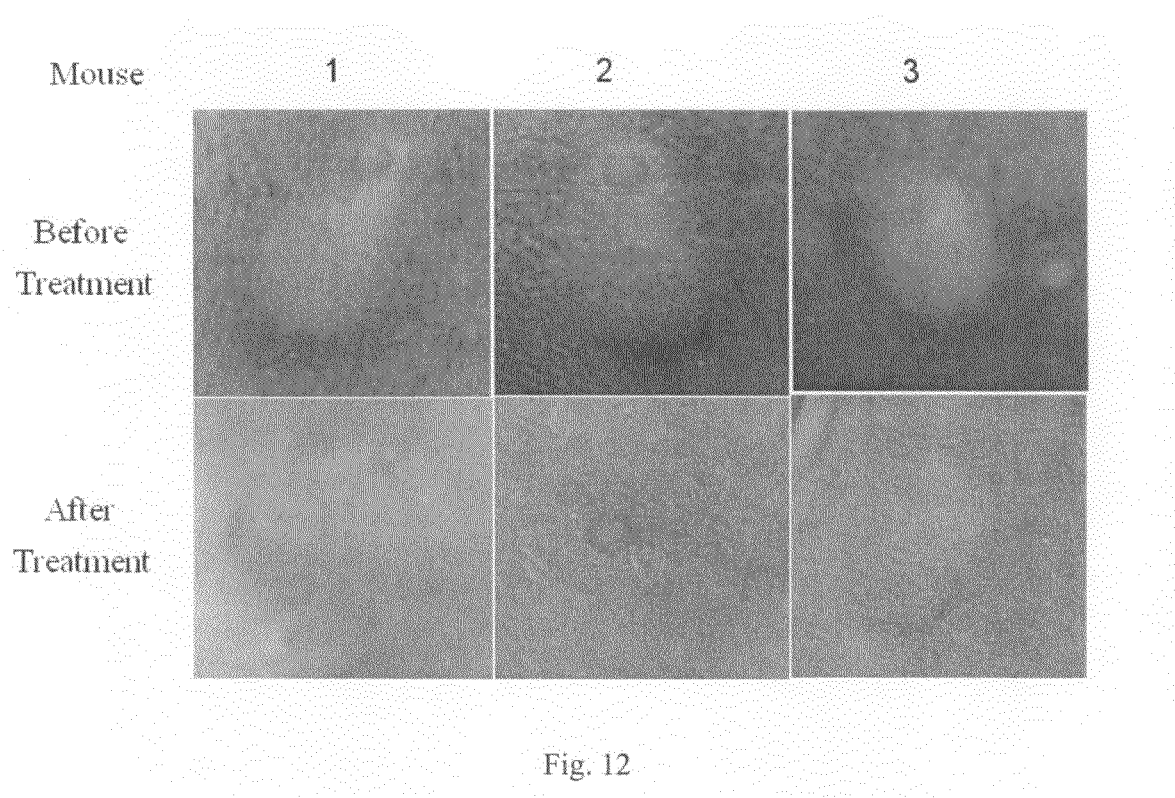
FIG. 12 shows pictures depicting the size reduction of breast cancer MCF7 cell xenografts in mice after treatment with Icaritin at 5 mg per mouse, once every other day for 15 days. Three representative tumors from three different mice before and after treatment were shown.

Tumor formation was assayed in female athymic nude mice (6 weeks old, strain CDI nu/nu, Charles River Breeding Laboratory). MCF7 cells or MDA-MB-231 cells at the concentration of $1 \times 10^7$ cells in 200 µl Matrigel (BD Biosciences) were injected into the mice by the mammary fatpad injection. A group of 5 mice were injected with each type of breast cancer cells. For MCF7 cells, inoculation was performed 5 days after subcutaneous implantation of 1.7 mg/60-day release E2β pellets (a slow release E2β pellet that can release a certain amount of E2β every day for 60 days) purchased from Innovative Research of American, Sarasota, Fla. Animals with tumor size about 0.5 cm in diameter were administered with Icaritin in corn oil using the gavage technique with an animal feeding needle. For the mice inoculated with MCF7 cells, each was feed with 5 mg of Icaritin every other day for 15 days. For the mice inoculated with MDA-MB-231 cells, each was feed with 5 mg of Icaritin every other day for 30 days. Tumor disappearance was determined by palpation, and the sizes of tumors were also monitored by measuring two perpendicular diameters with vernier calipers every other day and photographed. FIGS. 11 and 12 show pictures of the tumor size reduction in MDA-MB-231 and MCF7 cell xenografts, respectively, before and after Icaritin treatment. The results show that there was a significant tumor size reduction in both types of breast cancer cell xenografts after Icaritin treatment.

Example 10

Figure 13:
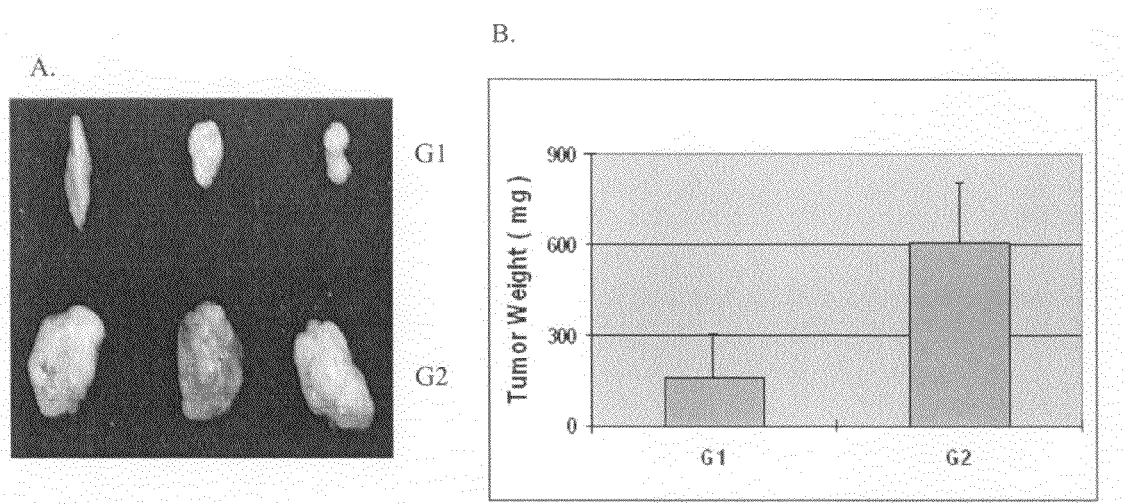
FIG. 13 shows (a) a picture showing the size of breast cancer MDA-MB-231 cell xenografts in mice after treatment with Icaritin at 1 mg per mouse, twice a week for 36 days, and (b) a histogram graph showing the weight change of the tumors with Icaritin treatment. The Icaritin treatment started right after the breast cancer cells were inoculated in the mice. G1: Tumors from mice treated with Icaritin. G2: Tumors from mice treated with corn oil.

Icaritin Inhibits Growth of ER-Negative Breast Cancer Xenografts in Nude Mice When Icaritin was Applied Right After the Implantation Tumor formation was assayed in female athymic nude mice (6 weeks old, strain CDI nu/nu, Charles River Breeding Laboratory). MDA-MB-231 cells at the concentration of $1 \times 10^7$ cells in 200 µl Matrigel (BD Biosciences) were injected into the mice by the mammary fatpad injection. A group of 5 mice were injected with the breast cancer cells. The mice were treated with Icaritin right after the injection. Each mouse was fed with 1 mg of Icaritin twice a week for 36 days. Then the mice were sacrificed and the tumor tissues were dissected from the mice, photographed and weighed. FIG. 13 shows the tumor size reduction in MDA-MB-231 cell xenografts treated with Icaritin.

Example 11

Figure 14A:
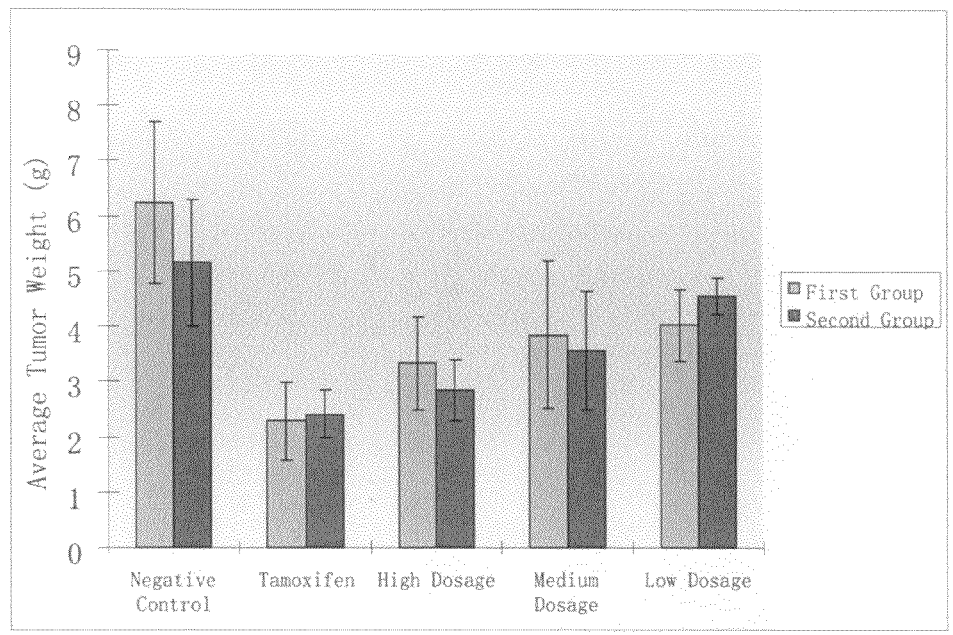
FIG. 14 shows (a) a histogram graph showing the average tumor weight and (b) a histogram graph showing the tumor growth inhibition rate of tumors in BALB/c-nu mice implanted with human breast cancer BCAP-37 cells wherein the mice were treated with Tamoxifen at 0.35 mg/mouse/day, Icaritin at 0.7 mg/mouse/day (high dosage), 0.35 mg/mouse/day (medium dosage) and 0.18 mg/mouse/day (low dosage), and 0.1 ml olive oil (negative control), respectively; and further shows (c) a histogram graph showing the average tumor weight and (d) a histogram graph showing the tumor growth inhibition rate of tumors in BALB/c-nu mice implanted with human breast cancer BCAP-37 cells wherein the mice were treated with Tamoxifen at 0.35 mg/mouse/day, IC163 at 0.7 mg/mouse/day, and the equivalent volume of olive oil (negative control), respectively.
Figure 14B:
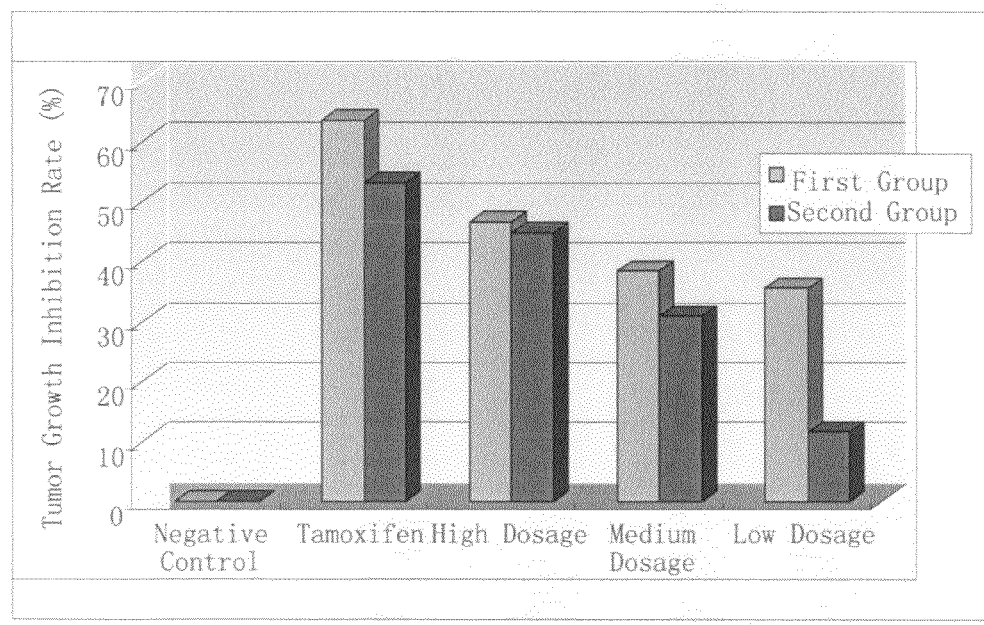

Icaritin and IC 163 Inhibits Growth of Human Breast Cancer BCAP-37 Cells Xenografts in Nude Mice Nude mice with breast cancer xenografts were treated with Icaritin to test its effect on inhibiting tumor growth. The original nude mice bearing BCAP-37 breast cancer were provided by the Institute of Materia Medica, Chinese Academy of Medical Sciences. Tumor tissues were taken from the mice and cut into small pieces. Several pieces of the tumor tissues were implanted into the armpit under the right front limb of female nude mice (provided by the Division of Experimental Animals of the Medical School of Beijing University). After the implantation, the mice were fed with E2β solution once every day at the dosage of 7 µg per mouse for 6 days to stimulate tumor growth in the receiving mice. Starting on the seventh day, the mice were fed with Icaritin at three dosages. The high dosage was 0.7 mg per mouse per day (about 33 mg/kg/day). The medium dosage was 0.35 mg per mouse per day (about 16.5 mg/kg/day). The low dosage was 0.18 mg per mouse per day (about 8.25 mg/kg/day). Tamoxifen was used at the dosage of 0.35 mg per mouse per day as a positive control. Olive oil was used as a negative control wherein each mouse was fed with 0.1 ml of olive oil. Icaritin was prepared as an olive oil solution by the same method as described in Example 9 above. The mice were given Icaritin at the different dosages, Tamoxifen or olive oil once every day for 15 days. Then the mice were sacrificed and the tumor tissues were dissected from the mice and weighed. Two parallel experiments were done for the tests. Ten female BALB/c-nu mice were used for each test compounds and each dosages for one of the two parallel experiment. Eight female BALB/c-nu mice were used for each test compounds and each dosages for the other parallel experiment. FIG. 14a shows that mice treated with Icaritin at the high, medium and low dosages had reduced tumor weights when compared with the negative controls. FIG. 14b shows the tumor growth inhibition rates at the different dosages. The tumor growth inhibition rate is a percentage calculated using the formula: tumor growth inhibition rate=(average weight of the tumor in the control−average weight of the tumor treated with Icaritin)/average weight of the tumor in the control. The tumor weight in mice treated with the high dosage of Icaritin had a similar tumor weight reduction as the positive control.

Figure 14C:
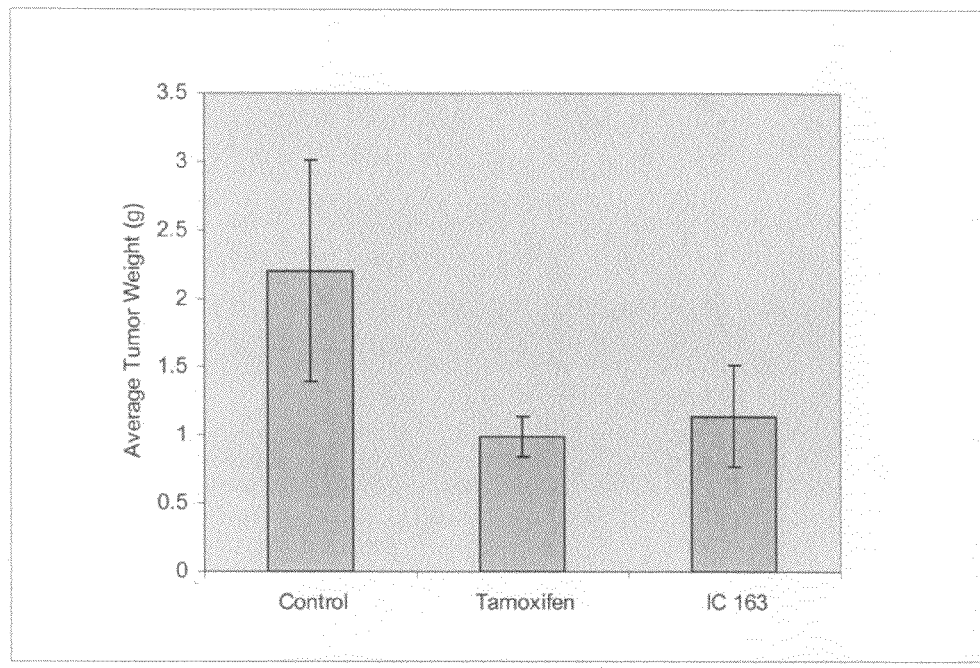
Figure 14D:
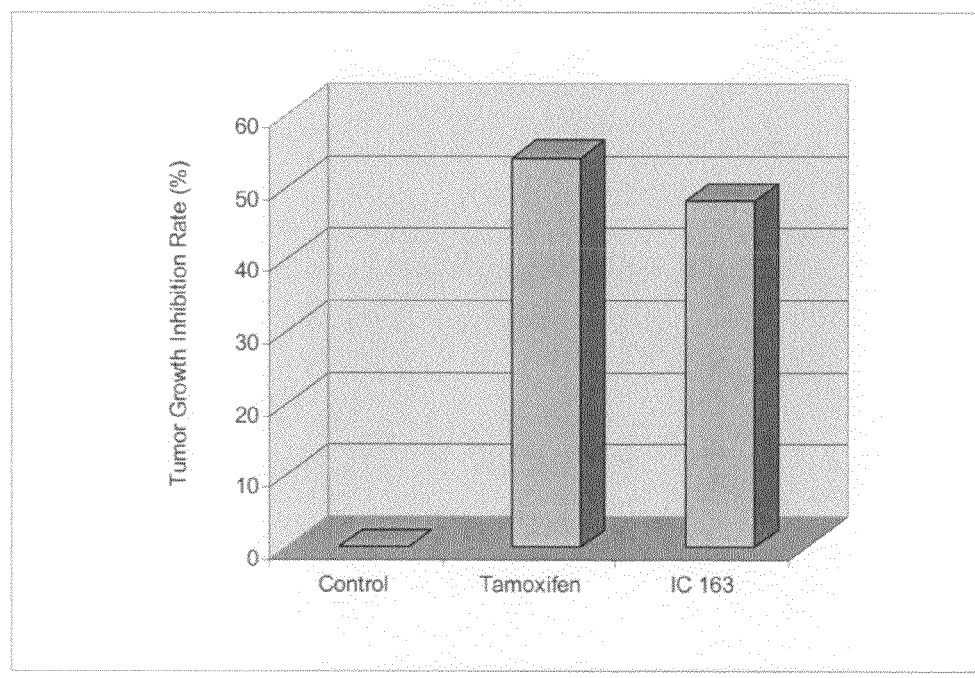

The effect of IC 163 on inhibiting breast cancer growth was tested in the same assay as described above. IC 163 was tested at the dosage of 0.7 mg per mouse per day (about 35 mg/kg/day). Tamoxifen was tested at half of the dosage of IC 163 as a positive control. Olive oil was used as a negative control. FIGS. 14c and 14d show that IC 163 treatment had a similar effect as Tamoxifen in inhibiting tumor growth.

Example 12

Figure 15A:
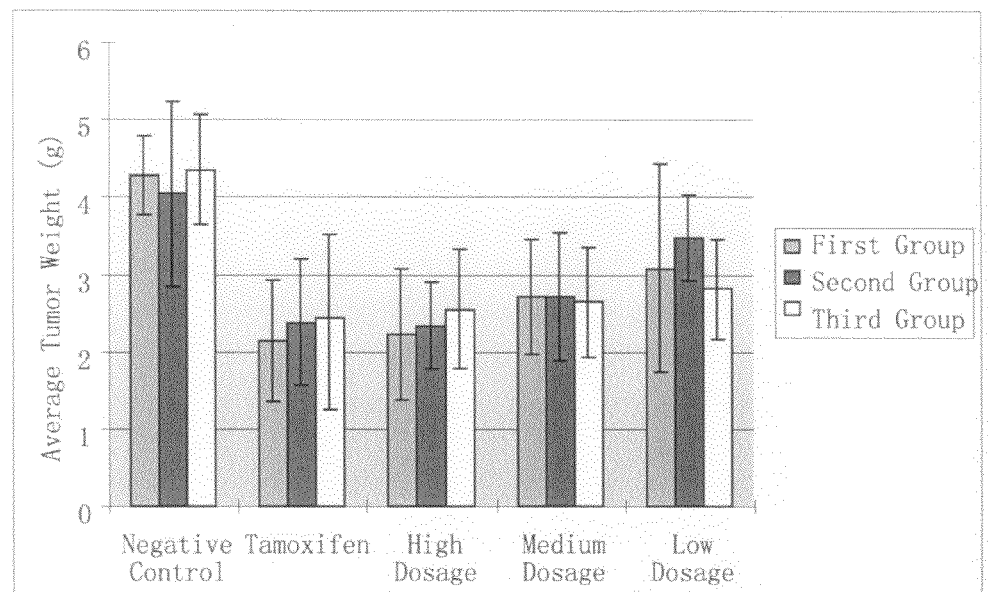
FIG. 15 is (a) a histogram graph showing the average tumor weight and (b) a histogram graph showing the tumor growth inhibition rate of tumors in ICR mice implanted with cervical cancer U14 cells wherein the mice were treated with Tamoxifen at 0.35 mg/mouse/day, Icaritin at 0.7 mg/mouse/day (high dosage), 0.35 mg/mouse/day (medium dosage) and 0.18 mg/mouse/day (low dosage), and 0.1 ml olive oil (negative control), respectively.
Figure 15B:
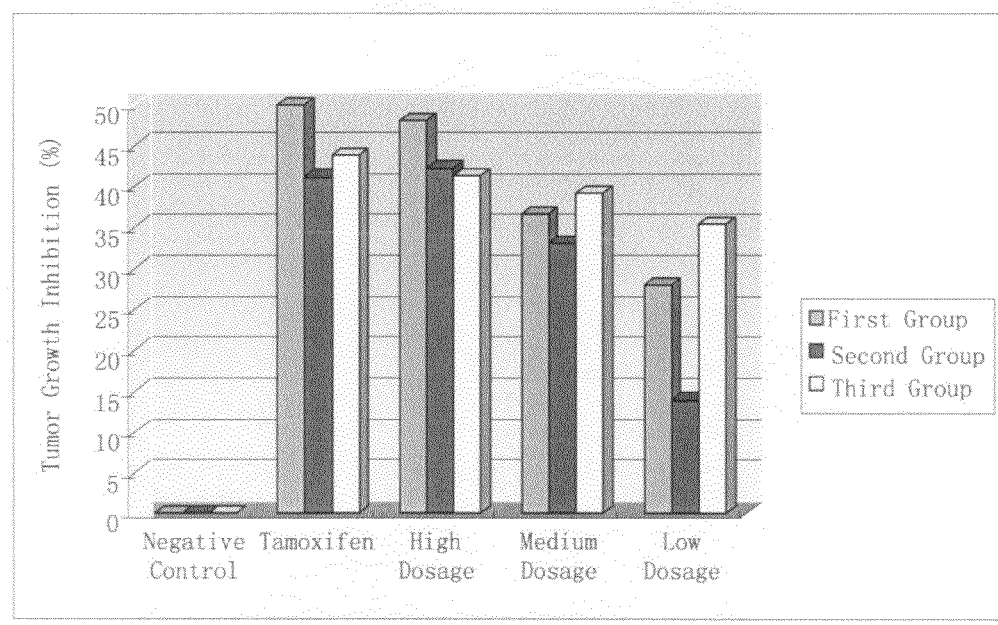

Icaritin Inhibits Growth of Murine Cervical Cancer U14 Cells Xenografts in ICR Mice The original ICR mice containing cervical cancer U14 cell line were provided by the Institute of Materia Medica, Chinese Academy of Medical Sciences. Five ml of abdominal fluid was drawn from the lower abdomen of the mice. The fluid was diluted at the ratio of 1:5 with saline. 0.2 ml of the diluted abdominal fluid was injected subcutaneously at the right front limb and chest of female ICR mice (provided by the Division of Experimental Animals of the Medical School of Beijing University). After the implantation, the mice were treated right away with Icaritin, Tamoxifen and olive oil, respectively. Icaritin was given at three dosages. The high dosage was 0.7 mg per mouse per day (about 33 mg/kg/day). The medium dosage was 0.35 mg per mouse per day (about 16.5 mg/kg/day). The low dosage was 0.18 mg per mouse per day (about 8.25 mg/kg/day). Tamoxifen was used at the dosage of 0.35 mg per mouse per day (about 16.5 mg/kg/day) as a positive control. Olive oil was used as a negative control wherein each mouse was fed with 0.1 ml of olive oil. Icaritin was prepared as an olive oil solution by the same method as described in Example 9 above. The mice were given Icaritin at different dosages, Tamoxifen or olive oil once every day for a period of 14 days. Then the mice were sacrificed and the tumor tissues were dissected from the mice and weighed. Ten female ICR mice were used for each test compounds and dosages. Three parallel experiments were carried out. FIG. 15*a* shows that ICR mice treated with Icaritin at the high, medium and low dosages had reduced tumor weights when compared with the negative control. The tumor weight in mice treated with the high dosage of Icaritin had a similar tumor weight reduction as the positive control. FIG. 15*b* shows the tumor growth inhibition rates at the different dosages. The tumor growth inhibition rate was calculated using the same formula as Example 11.

Example 13

IC 163 Induces Cell Death in Breast, Lung and Prostate Cancer Cells

Figure 16:
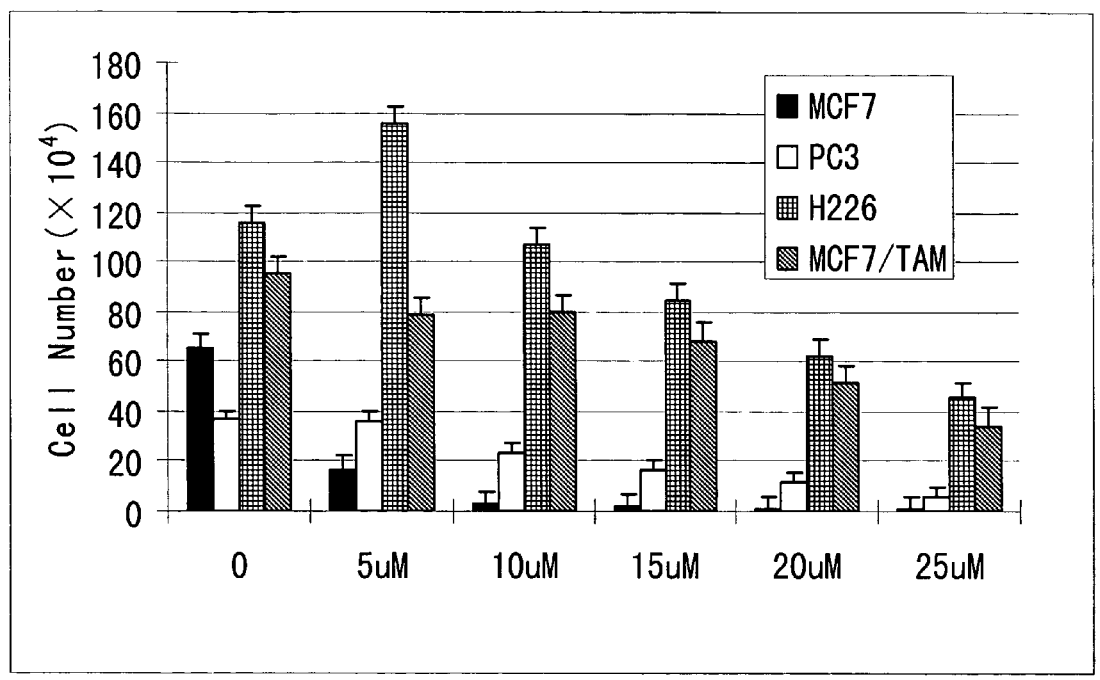
FIG. 16 is a histogram graph showing the numbers of surviving cells after MCF7, PC3 prostate cancer cells, H226 Lung Cancer Cells, and Tamoxifen resistant MCF7 cells were treated with IC 163 at concentrations from zero to 25 μM.

MCF7 cells, PC3 prostate cancer cells, H226 Lung Cancer Cells and MCF7/TAM cells were treated with IC 163 to test the effect of the compound on inhibiting cancer cell growth. The experiments were conducted in the same way as in Example 8. The results are shown in FIG. 16. At 5 µM, the numbers of cells of some cell lines started to decrease. At 10 µM, the numbers of cells of all tested cell lines were reduced and continued to reduce as the concentration of IC 163 increased.

Example 14

The Effect of IC-163 on Deterring Asthma Attack Induced by Ovalbumin in Guinea Pigs Guinea pigs of 250-300 g were provided by Beijing Haidian Xingwang Animal Farm. The guinea pigs were injected with 1 ml 10% ovalbumin (Sigma Cat. No. A5253) into abdomen once. On the 15th-17th day after the injection, the guinea pigs were given 1% aerosolized ovalbumin for about 20 seconds through nasal spray to induce asthma attack. The latent period before asthma attack calculated from after ovalbumin administration to the time when the guinea pigs collapsed with convulsion was measured. If a guinea pig did not collapse with convulsion within 150 seconds after the ovalbumin administration, that guinea pig was disqualified from further testing.

On the 17th day after injection, the qualified guinea pigs were divided into 3 groups, the high dosage IC-163 group (4 mg/kg/day), the low dosage IC-163 group (1 mg/kg/day) and the control group. Each group consisted of 10 guinea pigs. A normal group consisting of 8 normal guinea pigs which had not been injected with any 10% ovalbumin was also tested. IC-163 was administered to the guinea pigs at 4 mg per kilogram of body weight per day (the high dosage group) or 1 mg per kilogram of body weight per day (the low dosage group) through muscle injection once a day for 6 days while the guinea pigs of the normal group and the control group were injected with saline water. On the 4th and 6th day of administering the drug, the guinea pigs were induced for asthma attack in the same way as above. The latent period before asthma attack was measured. If the latent period lasted longer than 5 minutes, the latent period was recorded as 5 minutes. On the 6th day, blood was drawn from the guinea pigs of the four groups to examine the percentage of oxyphil cells, the concentrations of histamine and IgE in the blood. The percentage of oxyphil cells was measured by counting the number of oxyphil cells in every 200 leukocytes under microscope. The concentrations of histamine and IgE were measured by double-antibody sandwich ELISA (Enzyme Linked Immunosorbent Assay).

Figure 17:
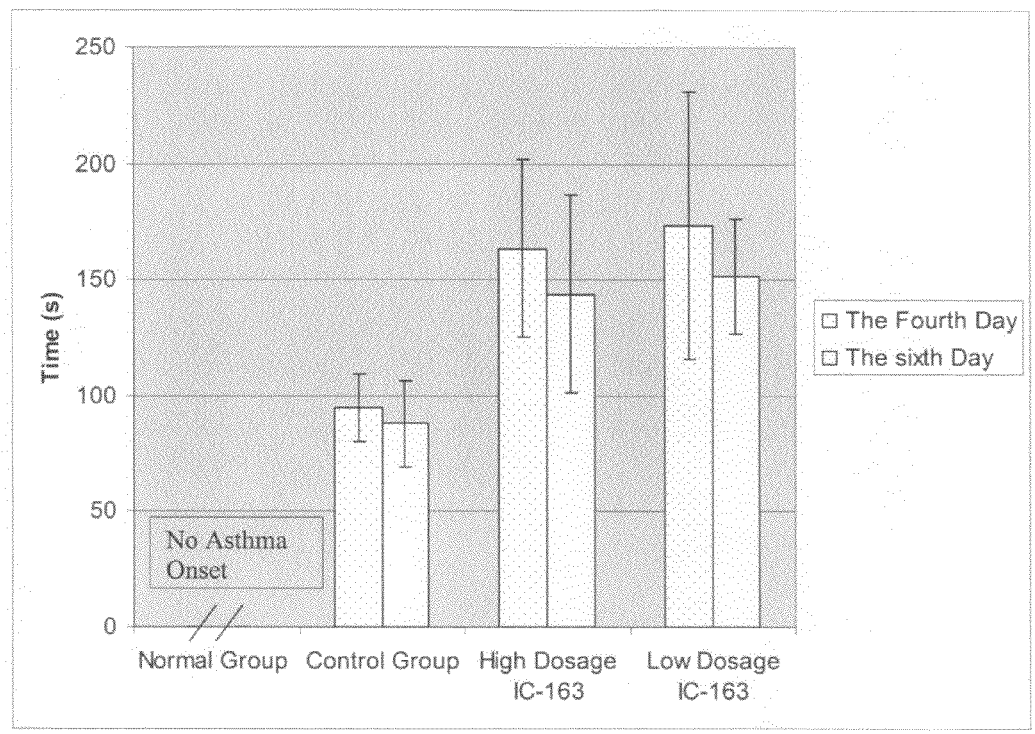
FIG. 17 is a histogram graph showing the latent period before asthma attack induced by ovalbumin at the 4th and 6th day of administering high dosage (4 mg/kg/day) and low dosage (1 mg/kg/day) of IC-163.

FIG. 17 shows the latent period before asthma attack induced by ovalbumin on the 4th and 6th day of administering high and low dosages of IC-163 into guinea pigs. When high dosage of IC-163 was administered, the latent period was extended by 72.9% on the 4th day of drug administration, and 63.5% on the 6th day, in comparison with the control group. When low dosage of IC-163 was administered, the latent period was extended by 83.4% on the 4th day and 72.7% on the 6th day in comparison with the control group. The results showed that the administration of high and low dosages of IC-163 could significantly delay asthma attack in guinea pigs induced by ovalbumin.

Figure 18:
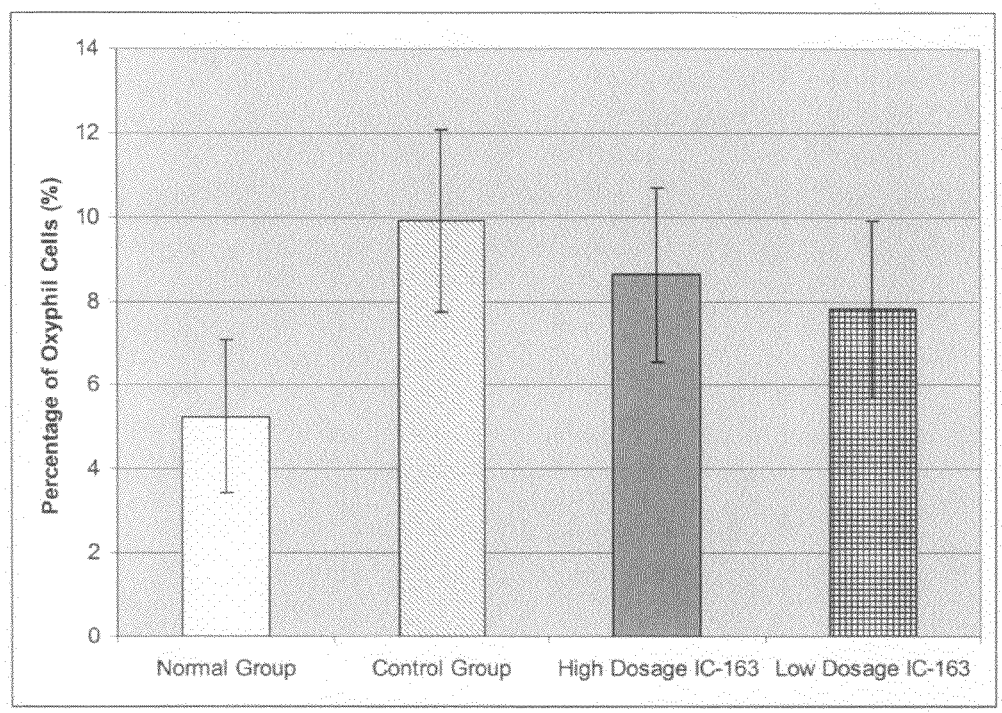
FIG. 18 is a histogram graph showing the percentage of oxyphil cells in the blood of tested guinea pigs on the 6th day of administering high dosage (4 mg/kg/day) and low dosage (1 mg/kg/day) of IC-163.

FIG. 18 shows the percentage of oxyphil cells in the blood when the guinea pigs were administered with high and low dosages of IC-163. The percentage of oxyphil cells of the normal group was about 5.3% while the percentage of control group was as high as about 9.9%. When IC-163 was administered at the high and low dosages, the percentages of oxyphil cells were reduced to about 8.6% and about 7.8%, respectively. The figure indicates that the high and low dosages of IC-163 can significantly reduce the percentage of oxyphil cells in the tested guinea pigs.

Figure 19:
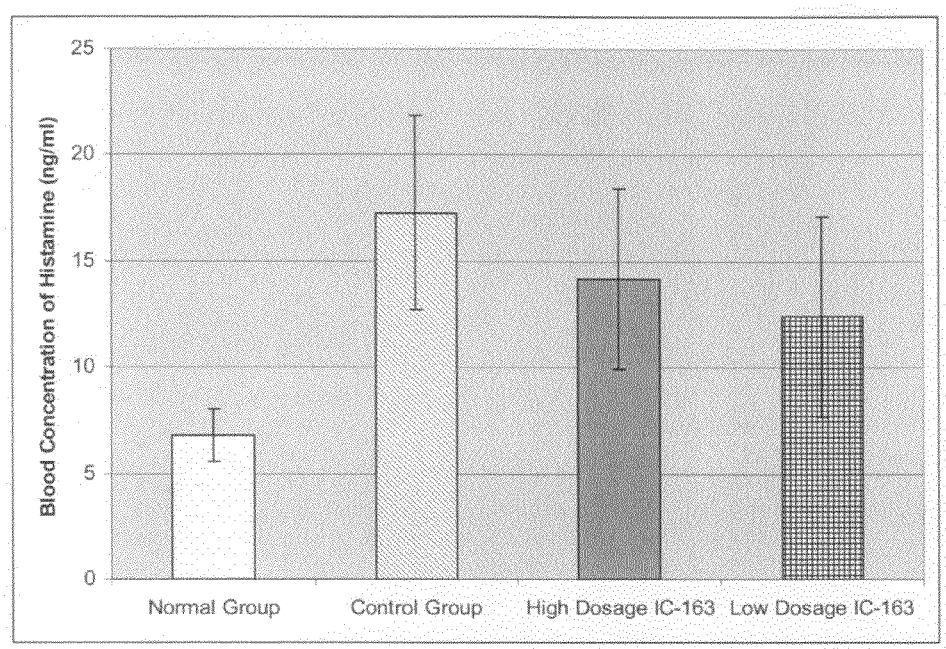
FIG. 19 is a histogram graph showing the blood concentration of histamine in tested guinea pigs on the 6th day of administering high dosage (4 mg/kg/day) and low dosage (1 mg/kg/day) of IC-163.

The concentration of Histamine in the blood of guinea pigs was measured in the normal group, control group, the high dosage IC-163 and low dosage IC-163 groups. The results in FIG. 19 showed that administration of high and low dosages of IC-163 could significantly reduce the blood concentrations of histamine in guinea pigs.

Figure 20:
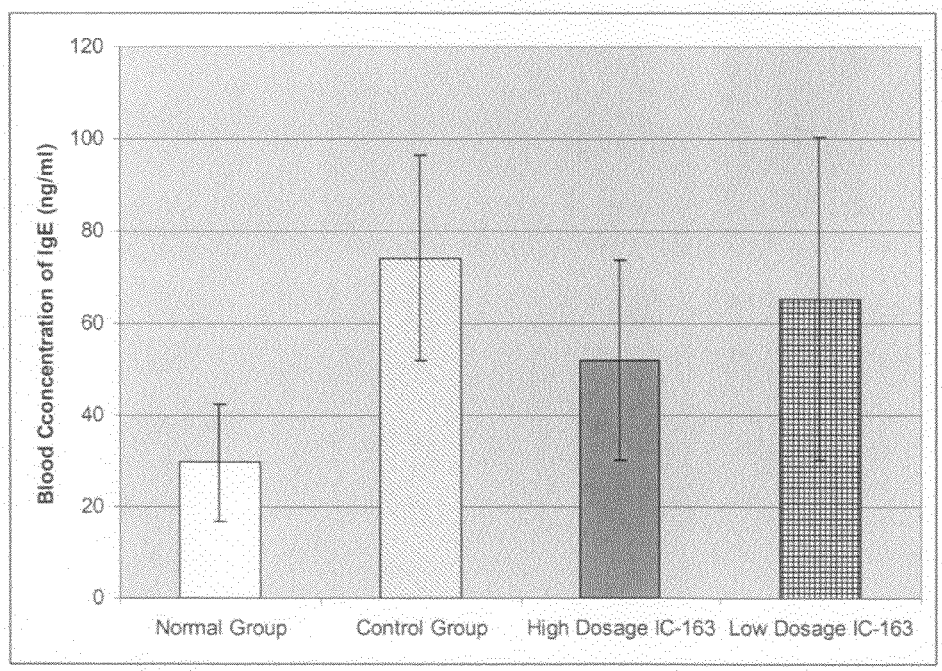
FIG. 20 is a histogram graph showing the blood concentration of IgE in the blood of tested guinea pigs on the 6th day of administering high dosage (4 mg/kg/day) and low dosage (1 mg/kg/day) of IC-163.

The concentration of IgE in the blood of guinea pigs of the four groups was also measured and the results were shown in FIG. 20. The results showed that administration of the high and low dosages of IC-163 could significantly reduce the concentration of IgE in the tested guinea pigs.

Example 15

Icaritin Inhibits Growth of Human Endometrial Cancer Hec1A Cells

Human endometrial cancer Hec1A cells (ATCC No.: HTB-112™) were subseeded in a 96-well culture plate at a concentration of $5 \times 10^3$ cells/well and were cultured in DMEM containing high glucose medium (HyClone, SH30022.01B). Cells were serum-starved overnight and exposed to tamoxifen or icaritin at different concentrations for 24 hours. The concentration of tamoxifen or icaritin is 0 µM, 0.001 µM, 0.01 µM, 0.1 µM, 1 µM, 3 µM and 5 µM, respectively. The cells then were incubated with 0.5 mg/ml 3-(4,5-dimethylthiazol-2-yl)-2,5-diphenyltetrazolium bromide (MTT) for 4 hours at 37° C. wherein the MTT was reduced to insoluble purple formazan by the active mitochondrial reductase enzymes in the living cells. Then the excessive liquid MTT was removed from the reaction mixture. 150 µl of DMSO was added to dissolve the purple formazan into a colored solution. The optical density of the colored solution was measured at 490 nm using a microplate reader. The optical density of the colored solution had a linear relationship with the number of cells in the solution, enabling accurate quantification of the cells.

Figure 21:
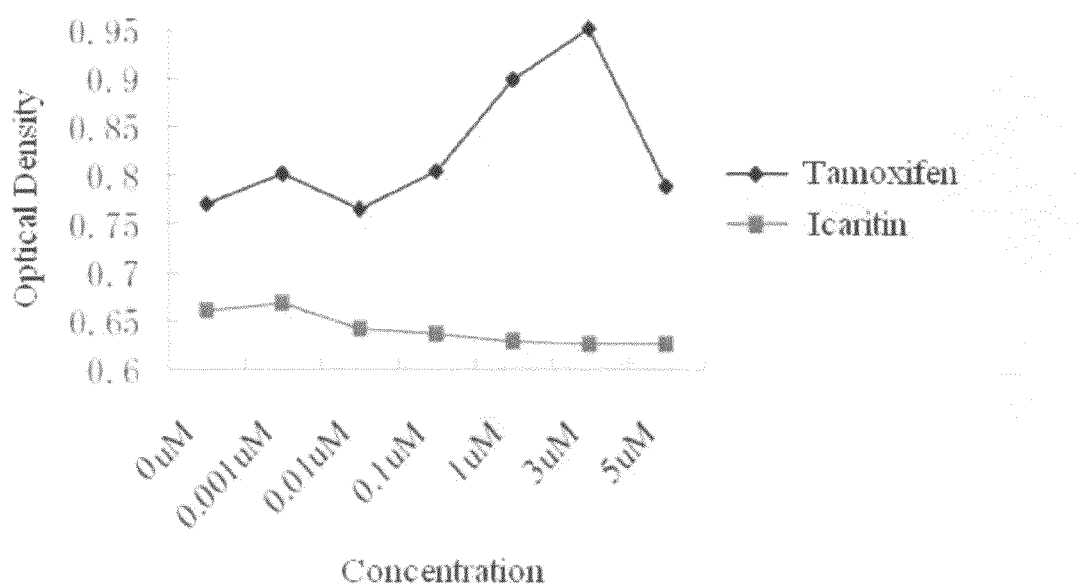
FIG. 21 is a line chart showing the optical density of color changes in solutions where the human endometrial cancer Hec1A cells were treated with tamoxifen or icaritin at different concentrations.

FIG. 21 shows the result of the MTT assay. The optical density declined smoothly when the Hec1A cells were exposed to icaritin at increased concentrations. On the contrary, the optical density rose when the Hec1A cells were exposed to tamoxifen at concentrations that increased from 0.001 µM to 3 µM. The figure indicates that icaritin has significant inhibitory effect on the growth of Hec1A cells while tamoxifen has the opposite effect of stimulating the growth of Hec1A cells at concentrations below 3 μM.

We claim:

1. A method of treating cancer or asthma involving abnormal proliferation of cells expressing ER-α36 in a subject in need thereof, comprising administering to the subject a therapeutically effective amount of a pharmaceutical composition comprising Icaritin;
   wherein Icaritin has a structure of 3,5,7-trihydroxy-2-(4-methoxyphenyl)-8-(3-methylbut-2-enyl)-4H-chromen-4-one,
   wherein Icaritin is administered to the subject at a dosage in the range of 0.01 mg to 100 mg per kilogram body mass of the subject; and
   wherein Icaritin reduces abnormal proliferation of the cells expressing ER-α36.

2. The method of claim 1 wherein the subject is mammal.

3. The method of claim 2 wherein the mammal is human.

4. The method of claim 1 wherein the administering is oral, buccal, sublingual, ocular, topical, parenteral, rectal, intracisternal, intravaginal, intraperitoneal, intravesical, or nasal.

5. The method of claim 4 wherein the administering is parenteral.

6. The method of claim 1 wherein the disease is breast cancer.

7. The method of claim 1 wherein Icaritin is administered to the subject at a dosage in the range of 0.1 mg to 100 mg per kilogram of body mass of the subject.

8. The method of claim 1 wherein Icaritin is administered to the subject at a dosage in the range of 0.5 mg to 100 mg per kilogram of body mass of the subject.

9. The method of claim 1 wherein Icaritin is administered to the subject at a dosage in the range of 1 mg to 100 mg per kilogram of body mass of the subject.

10. The method of claim 9 wherein Icaritin is administered to the subject at a dosage in the range of 1 mg to 75 mg per kilogram of body mass of the subject.

11. The method of claim 9 wherein Icaritin is administered to the subject at a dosage in the range of 1 mg to 50 mg per kilogram of body mass of the subject.

12. The method of claim 1, wherein the disease is selected from the group consisting of breast cancer, cervix cancer, lung cancer, prostate cancer, and asthma.

13. The method of claim 1, wherein the disease is endometrial cancer.

14. The method of claim 1, wherein the disease is liver cancer or leukemia.

* * * * *